(12) United States Patent
Xiao et al.

(10) Patent No.: US 9,725,439 B2
(45) Date of Patent: Aug. 8, 2017

(54) QUINAZOLINE DERIVATIVE AND PREPARATION METHOD THEREFOR

(71) Applicants: CHIA TAI TIANQING PHARMACEUTICAL GROUP CO., LTD., Lianyungang (CN); CENTAURUS BIOPHARMA CO., LTD., Beijing (CN); LIANYUNGANG RUNZHONG PHARMACEUTICAL CO., LTD., Lianyungang (CN)

(72) Inventors: Dengming Xiao, Beijing (CN); Yan Zhu, Beijing (CN); Yuandong Hu, Beijing (CN); Huting Wang, Beijing (CN); Jijun Li, Beijing (CN); Yong Peng, Beijing (CN); Hui Zhang, Beijing (CN); Hong Luo, Beijing (CN); Fansheng Kong, Beijing (CN); Yongxin Han, Beijing (CN)

(73) Assignees: CHIA TAI TIANQING PHARMACEUTICAL GROUP CO., LTD., Jiangsu (CN); CENTAURUS BIOPHARMA CO., LTD., Beijing (CN); LIANYUNGANG RUNZHONG PHARMACEUTICAL CO., LTD., Jiangsu (CN)

( * ) Notice: Subject to any disclaimer, the term of this patent is extended or adjusted under 35 U.S.C. 154(b) by 0 days.

(21) Appl. No.: 15/024,472

(22) PCT Filed: Sep. 28, 2014

(86) PCT No.: PCT/CN2014/087633
§ 371 (c)(1),
(2) Date: Mar. 24, 2016

(87) PCT Pub. No.: WO2015/043515
PCT Pub. Date: Apr. 2, 2015

(65) Prior Publication Data
US 2016/0214964 A1 Jul. 28, 2016

(30) Foreign Application Priority Data
Sep. 28, 2013 (CN) .......................... 2013 1 0452885

(51) Int. Cl.
C07D 403/12 (2006.01)
C07D 401/14 (2006.01)
C07D 405/14 (2006.01)
C07D 401/12 (2006.01)

(52) U.S. Cl.
CPC ......... *C07D 403/12* (2013.01); *C07D 401/12* (2013.01); *C07D 401/14* (2013.01); *C07D 405/14* (2013.01)

(58) Field of Classification Search
CPC .................................................. C07D 401/12
See application file for complete search history.

(56) References Cited

U.S. PATENT DOCUMENTS

| 6,344,455 | B1 | 2/2002 | Bridges et al. |
| 2005/0085495 | A1 | 4/2005 | Soyka et al. |
| 2007/0027170 | A1 | 2/2007 | Soyka |
| 2010/0179120 | A1 | 7/2010 | Lee et al. |

FOREIGN PATENT DOCUMENTS

| CA | 2432428 A1 | 6/2002 |
| CN | 1330642 A | 1/2002 |
| CN | 1481370 A | 3/2004 |
| CN | 1867564 A | 11/2006 |
| CN | 1882569 A | 12/2006 |
| CN | 101003514 A | 7/2007 |
| CN | 101679384 A | 3/2010 |
| JP | 2002-530386 A | 9/2002 |
| JP | 2004-516283 A | 6/2004 |
| JP | 2007-510624 A | 4/2007 |
| JP | 2010-529115 A | 8/2010 |
| WO | WO00/31048 A1 | 6/2000 |
| WO | 02/50043 A1 | 6/2002 |
| WO | WO02/50043 A1 | 6/2002 |

(Continued)

OTHER PUBLICATIONS

International Search Report for PCt/CN2014/087633 dated Dec. 31, 2014. 6 pages.

(Continued)

*Primary Examiner* — Paul V Ward
(74) *Attorney, Agent, or Firm* — Fish & Richardson P.C.

(57) ABSTRACT

The present invention relates to a quinazoline derivative shown in formula (I) and a preparation method therefor, a pharmaceutical composition comprising the compound shown in formula (I), and an application of the compound in preparing drugs for curing and preventing tumors. The compound of the present invention can irreversibly prevent EGFR phosphorylation, and effectively depress signal transduction of cancer cells, and accordingly has higher anti-tumor activity in vitro and in vivo.

(I)

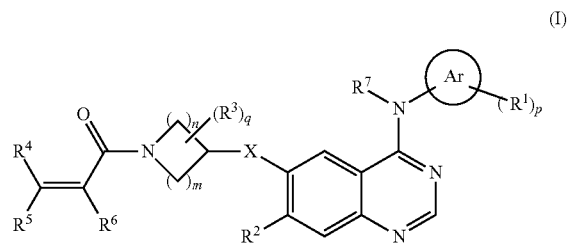

16 Claims, No Drawings

(56) References Cited

FOREIGN PATENT DOCUMENTS

| WO | WO2005/037824 A2 | 4/2005 |
|----|------------------|--------|
| WO | 2007/055513 A1   | 5/2007 |
| WO | WO2007/055513 A1 | 5/2007 |
| WO | 2008/002039 A    | 1/2008 |
| WO | WO2008/002039 A1 | 1/2008 |
| WO | WO2008/150118 A2 | 12/2008 |
| WO | 2013/042006 A1   | 3/2013 |
| WO | 2013/051883 A2   | 4/2013 |

OTHER PUBLICATIONS

Office Action issued by SIPO on Nov. 11, 2016 in corresponding Chinese Patent Application No. 2014800480740 (7 pages).
Japanese Patent Office Action issued on Jan. 17, 2017 in corresponding Japanese Patent Application No. 2016-544710 (3 pages).
Kim, E., et al., "Metabolite identification of a new tyrosine kinase inhibitor, HM781-36B, and a pharmacokinetic study by liquid chromatography/tandem mass spectrometry," Rapid Communications in Mass Spectrometry, vol. 27, No. 11, pp. 1183-1195 (2013).
Smaill, J.B., et al., "Tyrosine Kinase Inhibitors. 17. Irreversible Inhibitors of the Epidermal Growth Factor Receptor: 4-(Phenylamino)quinazoline- and 4- (Phenylamino )pyrido [3, 2-d]pyrimidine-6-acrylamides Bearing Additional Solubilizing Functions," Journal of Medicinal Chemistry 43:1380-1397 (2000).
European Patent Office, Extended European Search Report dated Mar. 27, 2017 in counterpart Chinese Patent Application No. 14849754.8 (12 pages).

QUINAZOLINE DERIVATIVE AND PREPARATION METHOD THEREFOR

TECHNICAL FIELD

The present disclosure relates to a quinazoline derivative and pharmaceutically acceptable salts thereof, preparation method thereof, pharmaceutical composition thereof, and the use in the prevention and treatment of tumor thereof.

BACKGROUND ART

Throughout the world, currently lung cancer is a malignant tumor with highest incidence and mortality. Lung cancer can be divided into two main types: small cell lung cancer and non-small cell lung cancer, where the non-small cell lung cancer accounts for 80% of the total amount of the lung cancer patients. The conventional chemotherapy and radiation therapy against non-small cell lung cancer lack specificity. Through these treatments, certain therapeutic effect is achieved and the lifespan of the patients is prolonged in some degree, however these treatments also bring about many side effects. Therefore targeted therapies, which can avoid excessive damage to normal cells, are more and more appreciated by the academia in the field of tumor and a wide range of patients. In the targeted therapies, epidermal growth factor receptor (EGFR) inhibitors play a significant role.

EGFR, a tyrosine kinase receptor, is a member of HER/ErbB family. The HER/ErbB family includes EGFR, HER2, HER3 and HER4, which are consist of three parts: an extracellular ligand-binding domain, a transmembrane domain consists of single chain, and a intracellular tyrosine kinase domain. EGFRs are widely distributed at the cell surface of the mammalian epithelial cells, fibroblasts, glial cells, keratinocytes, etc. The EGFR signaling pathway plays an important role in the physiological processes like cell growth, proliferation and differentiation, etc. The functional deficiency of protein tyrosine kinase like EGFR, or the abnormality in the activity or cellular localization of the key factors in the related signaling pathways, may all lead to occurrence of tumor, diabetes, immune deficiency and cardiovascular diseases.

So far the drugs related to EGFR available in the market includes: Gefitinib (Iressa®), Erlotinib (Tarceva®), which are selective EGFR tyrosine kinase inhibitors (EGFR-TKI); and Lapatinib (Tykerb®), which is an EGFR/HER2 dual inhibitor. They competitively bind the phosphorylation site of the tyrosine kinase at the intracellular segment to block the interaction between the phosphorylation site and ATP, and inhibit the phosphorylation of tyrosine and a series of downstream signal transduction, and then inhibit the growth of tumor cells. Among these drugs, the reversible EFGR inhibitor Gefitinib and Erlotinib show favorable therapeutic effects on non-small cell lung cancer patients with EGFR mutation; they can significantly prolong the progression-free survival (PFS) and overall survival (OS) of the patients. However, recent clinical use indicates that the PFS of most patients who are positive in EGFR mutation is no longer than 12~14 months, and soon afterwards develop resistance to the EGFR-TKIs mentioned above.

Current research showing that approximately half of the drug resistance generated after EGFR-TKI treatment relates to the secondary mutation (T790M) at exon 20 of EGFR. In this regard, several irreversible inhibitors, such as Afatinib (BIBW-2992), Canertinib (CI-1033), Neratinib (HKI-272), CO-1686, HM781-36B and the like are developed; they can solve the drug resistance problem of the EGFR-TKIs indicated above. These drug molecules share a common structural feature, that is, the existence of an acrylamide functional group. This functional group can form covalent bond with cysteine 773 (Cys733) at the ATP binding region of EGFR. Such covalent binding can irreversibly block the self phosphorylation of EGFR, and effectively inhibit the signal transduction of cancer cells. Therefore these drugs show higher in vitro and in vivo anti-tumor activity.

SUMMARY

The present disclosure provides a series of novel quinazoline derivatives or pharmaceutically acceptable salts thereof, and pharmaceutical composition comprising these compounds, and the method of using such compounds to prevent and treat tumor.

According to one aspect of the disclosure, the present disclosure provides a compound represented by formula (I) or a pharmaceutically acceptable salt thereof,

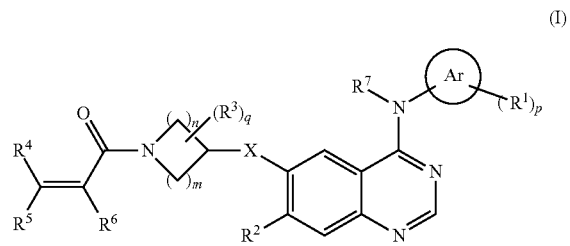

(I)

Where in the ring Ar is an aryl group or a heteroaryl group;

X is selected from —NR$^8$—, —S—, —S(=O)— or —S(=O)$_2$—;

n and m are each independently an integer of 0 to 6, and m, n are not simultaneously 0;

p is an integer of 0 to 5;

q is an integer of 0 to 8;

R$^1$ is independently selected from a C$_{1-6}$ alkyl group, a C$_{3-8}$ cycloalkyl group, a C$_{2-6}$ alkenyl group, a C$_{2-6}$ alkynyl group, a heterocycloalkyl group, a halogen atom, an amino group, a mono(C$_{1-6}$ alkyl) amino group, a di(C$_{1-6}$ alkyl) amino group, a hydroxy group, a C$_{1-6}$ alkoxy group, a mercapto group, a C$_{1-6}$ alkylthio group, a C$_{1-6}$ alkylcarbonyl group, an aryl group, a heteroaryl group, a cyano group, a nitro group, wherein the C$_{1-6}$ alkyl group, C$_{1-6}$ alkoxy group, C$_{2-6}$ alkenyl group, C$_{2-6}$ alkynyl group can be substituted by a halogen atom, a cyano group, a nitro group, a C$_{1-6}$ alkoxy group, an aryl group, a heteroaryl group or a heterocycloalkyl group; and the aryl group, heteroaryl group and heterocycloalkyl group can further be substituted by a halogen atom, a cyano group, a nitro group, a C$_{1-6}$ alkyl group, a C$_{1-6}$ alkoxy group, a C$_{1-6}$ alkylcarbonyl group;

R$^2$ is selected from hydrogen, a hydroxy group, a C$_{1-6}$ alkoxy group, a heterocycloalkyloxy group, or a C$_{1-6}$ alkoxy group substituted by C$_{1-6}$ alkoxy or heterocycloalkyl group;

R$^3$ is independently selected from a halogen atom, a cyano group, a mercapto group, a C$_{1-6}$ alkylthio group, a C$_{1-6}$ alkyl group, a C$_{3-8}$ cycloalkyl group, a heterocycloalkyl group, an amino group, a mono(C$_{1-6}$ alkyl) amino group, a di(C$_{1-6}$ alkyl) amino group, a hydroxy group, a C$_{1-6}$ alkoxy group, a C$_{1-6}$ alkoxycarbonyl group, a $C_{1-6}$ alkylamido group, a mono($C_{1-6}$ alkyl) aminoacyl group, a di($C_{1-6}$ alkyl)aminoacyl group;

$R^4$, $R^5$ and $R^6$ are each independently selected from hydrogen, a halogen atom, a $C_{1-6}$ alkyl group, a $C_{3-8}$ cycloalkyl group, a heterocycloalkyl group, an amino group, a mono($C_{1-6}$ alkyl) amino group, a di($C_{1-6}$ alkyl) amino group, a $C_{1-6}$ alkylamido group, a mono($C_{1-6}$ alkyl) aminoacyl group, a di($C_{1-6}$ alkyl) aminoacyl group, a $C_{1-6}$ alkoxycarbonyl group;

$R^7$, $R^8$ are each independently selected from hydrogen or a $C_{1-6}$ alkyl group.

In some embodiments of the present disclosure, X is selected from —$NR^8$—, —S—; in some embodiments of the present disclosure, X is —$NR^8$—.

In some embodiments of the present disclosure, n and m are each an integer of 0 to 3, and m, n are not simultaneously 0. In some embodiments of the present disclosure, n and m are each an integer of 0 to 3, and n+m=2, 3 or 4.

In some embodiments of the present disclosure, p is an integer of 0 to 3. In some embodiments, p is 1 or 2.

In some embodiments of the present disclosure, q is an integer of 0 to 3. In some embodiments, q is 0.

In some embodiments of the present disclosure, $R^7$, $R^8$ are hydrogen.

In some embodiments of the present disclosure, the ring Ar is a phenyl group.

In some embodiments of the present disclosure, $R^1$ is independently selected from a $C_{1-6}$ alkyl group, a $C_{2-6}$ alkenyl group, a $C_{2-6}$ alkynyl group, a halogen atom, an amino group, a hydroxy group, a $C_{1-6}$ alkoxy group, a $C_{1-6}$ alkylcarbonyl group, a cyano group, a nitro group, wherein the $C_{1-6}$ alkyl group, $C_{1-6}$ alkoxy group, $C_{2-6}$ alkenyl group, $C_{2-6}$ alkynyl group can be substituted by a halogen atom, a cyano group, a nitro group, a $C_{1-6}$ alkoxy group, an aryl group, a heteroaryl group or a heterocycloalkyl group; and the aryl group, heteroaryl group, heterocycloalkyl group can further be substituted by a halogen atom, a cyano group, a nitro group, a $C_{1-6}$ alkyl group, a $C_{1-6}$ alkoxy group, a $C_{1-6}$ alkylcarbonyl group.

In some embodiments of the present disclosure, $R^1$ is independently selected from a $C_{2-6}$ alkynyl group, a halogen atom, a $C_{1-6}$ alkoxy group, a $C_{1-6}$ alkylcarbonyl group, wherein the $C_{1-6}$ alkoxy group can be substituted by an aryl group, a heteroaryl group or a heterocycloalkyl group; and the aryl group, heteroaryl group, heterocycloalkyl group can further be substituted by a halogen atom, a cyano group, a nitro group.

In some embodiments of the present disclosure, $R^1$ is independently selected from a $C_{2-6}$ alkynyl group, a halogen atom, a heteroaryl-substituted $C_{1-6}$ alkoxy group, an aryl-substituted $C_{1-6}$ alkoxy group, a $C_{1-6}$ alkylcarbonyl group, wherein the aryl group, heteroaryl group can further be substituted by a halogen atom.

In some embodiments of the present disclosure, $R^1$ is independently selected from an ethynyl group, a halogen atom, a pyridyl-substituted $C_{1-6}$ alkoxy group, a halophenyl-substituted $C_{1-6}$ alkoxy group.

In some embodiments of the present disclosure, $R^4$, $R^5$ and $R^6$ are hydrogen.

In some embodiments of the present disclosure, $R^2$ is selected from hydrogen, a methoxy group, a tetrahydrofuranyloxy group, a methoxy-substituted ethoxy group, a morpholinyl-substituted ethoxy group.

Some embodiments of the present disclosure relate to the following compounds or salts thereof:

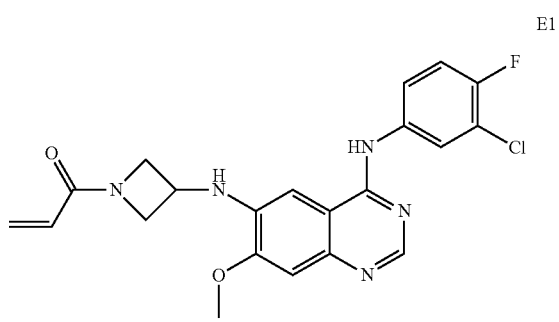

E1

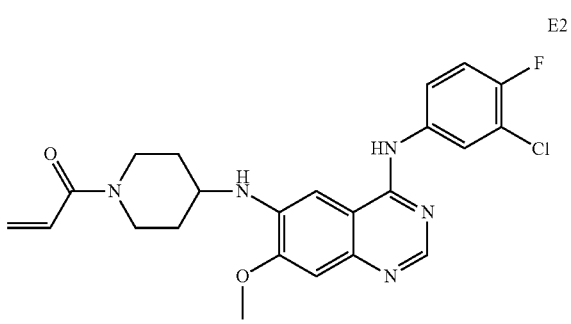

E2

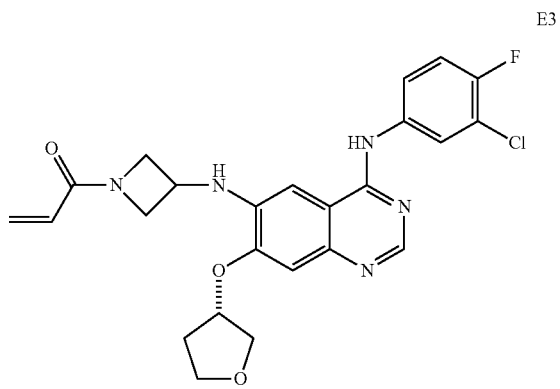

E3

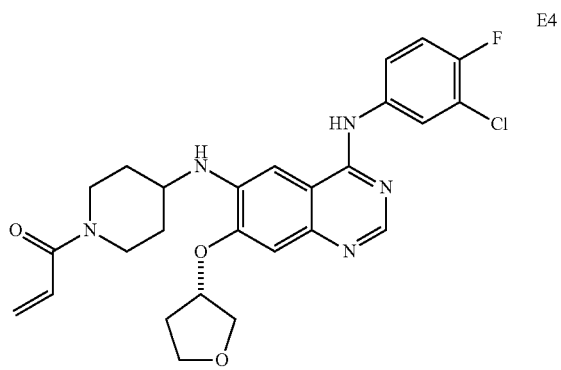

E4

-continued
E5
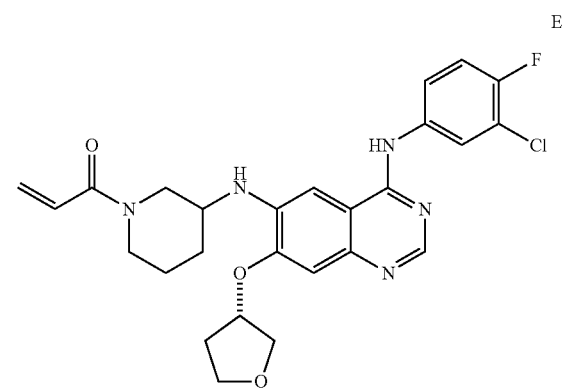
E6
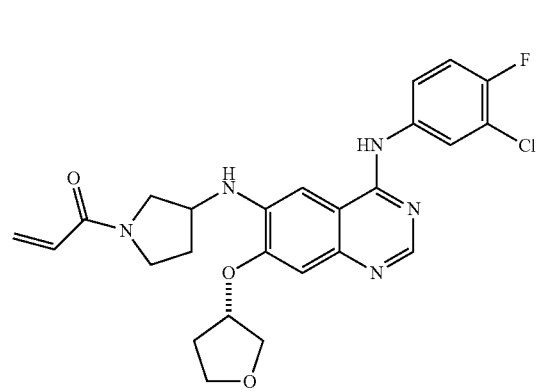
E7
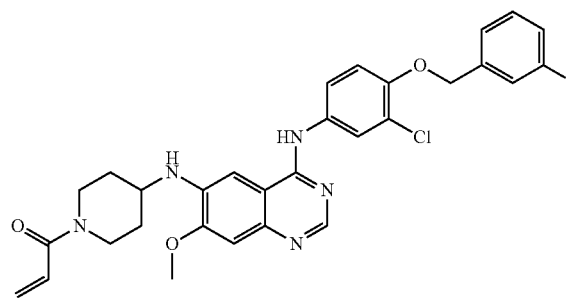
E8
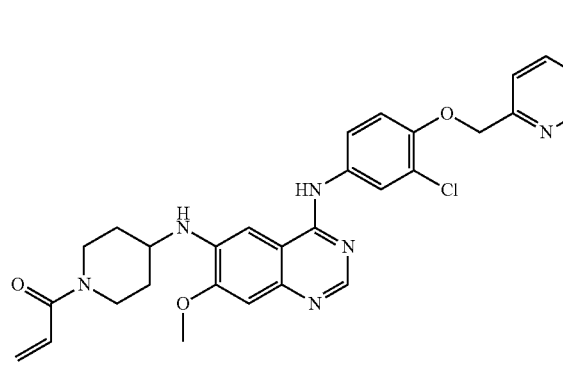
-continued
E9
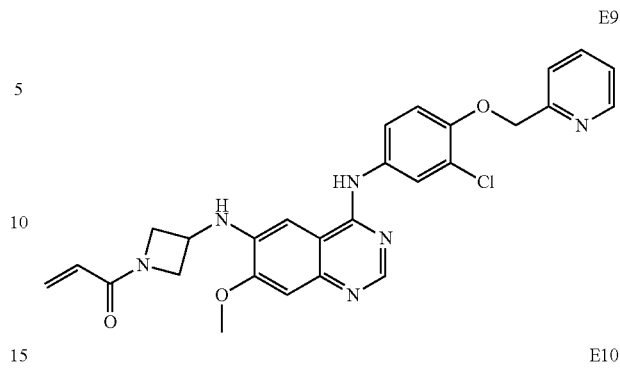
E10
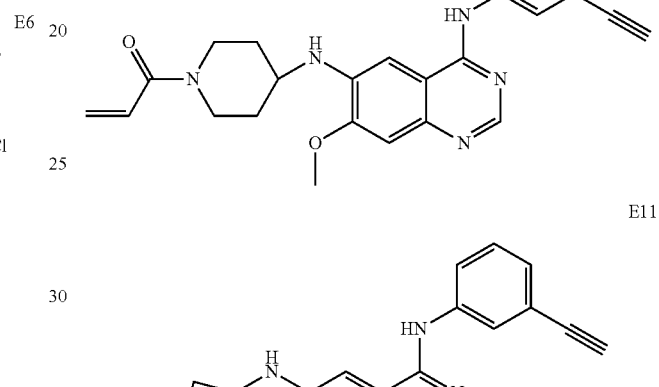
E11
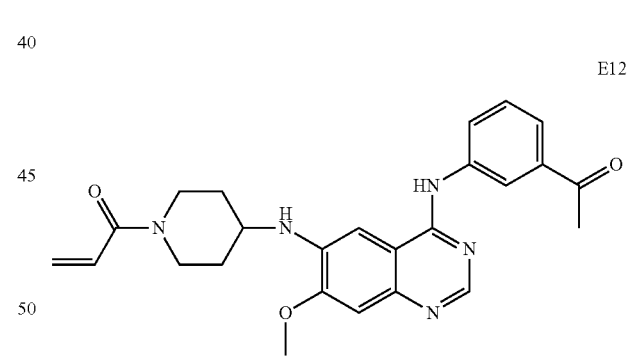
E12
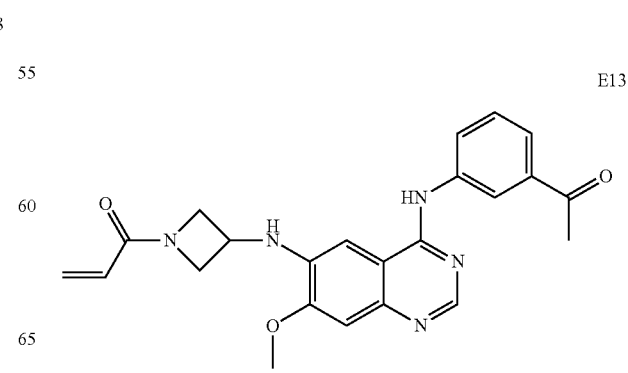
E13

E14
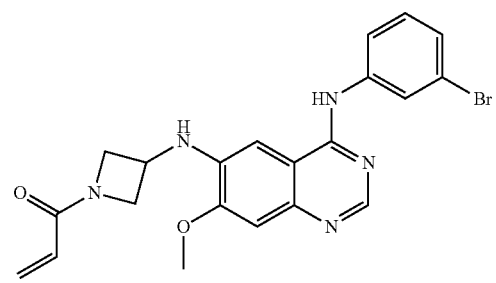
E15
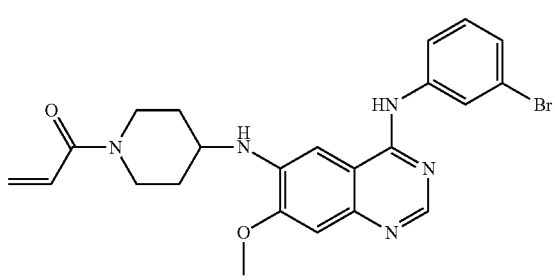
E16
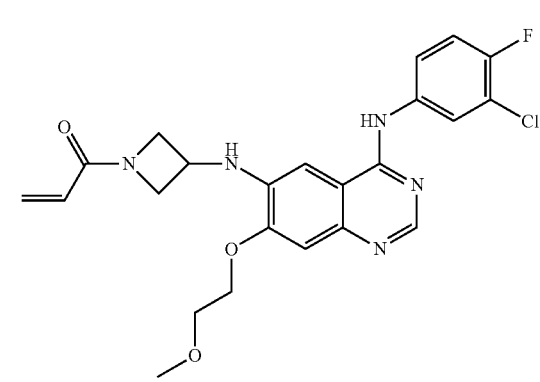
E17
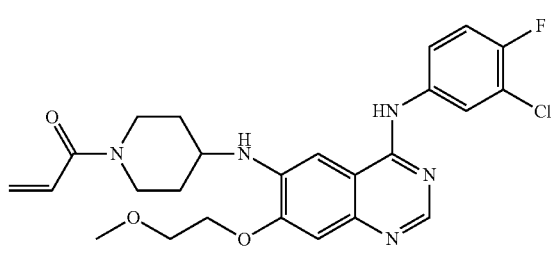
E18
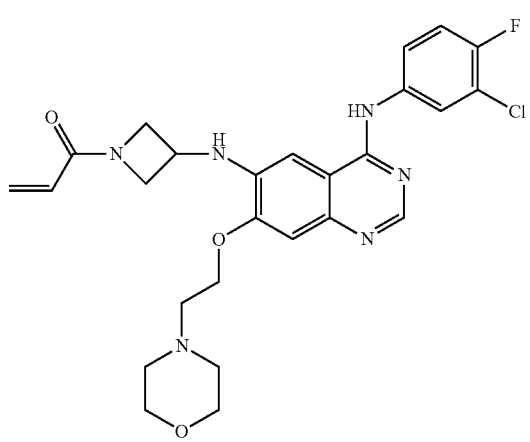
E19
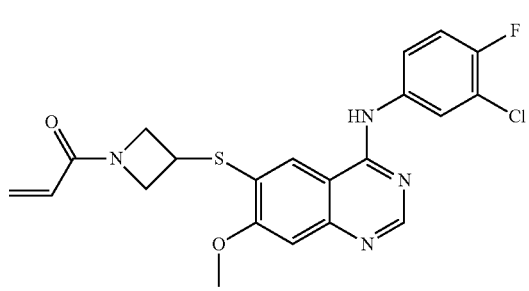
E20
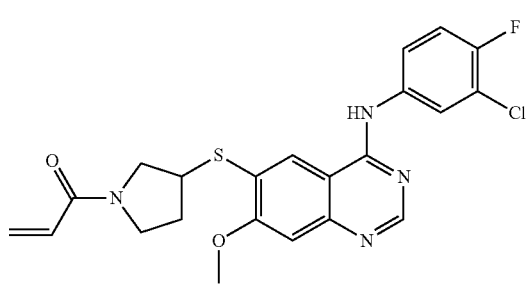
E21
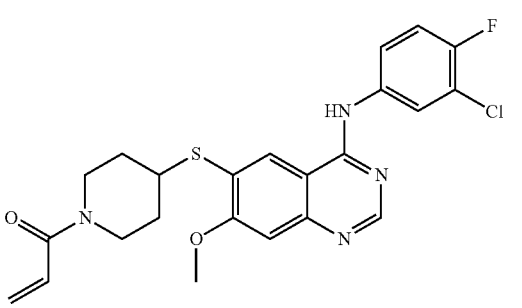
E22
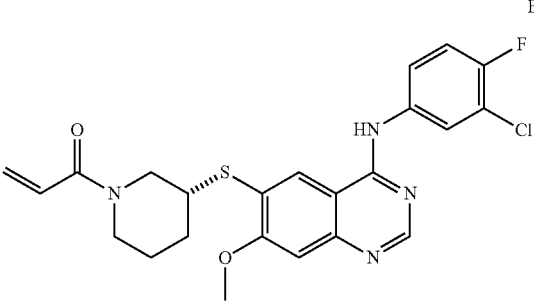

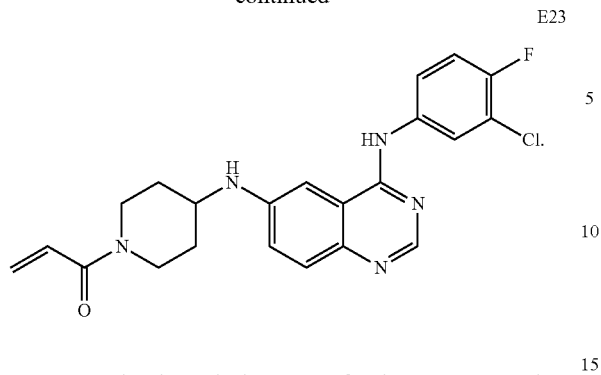
For example, through the steps of Scheme 1, 2 or other similar methods, the compound of formula (I) of the present disclosure can be prepared:
Scheme 1:
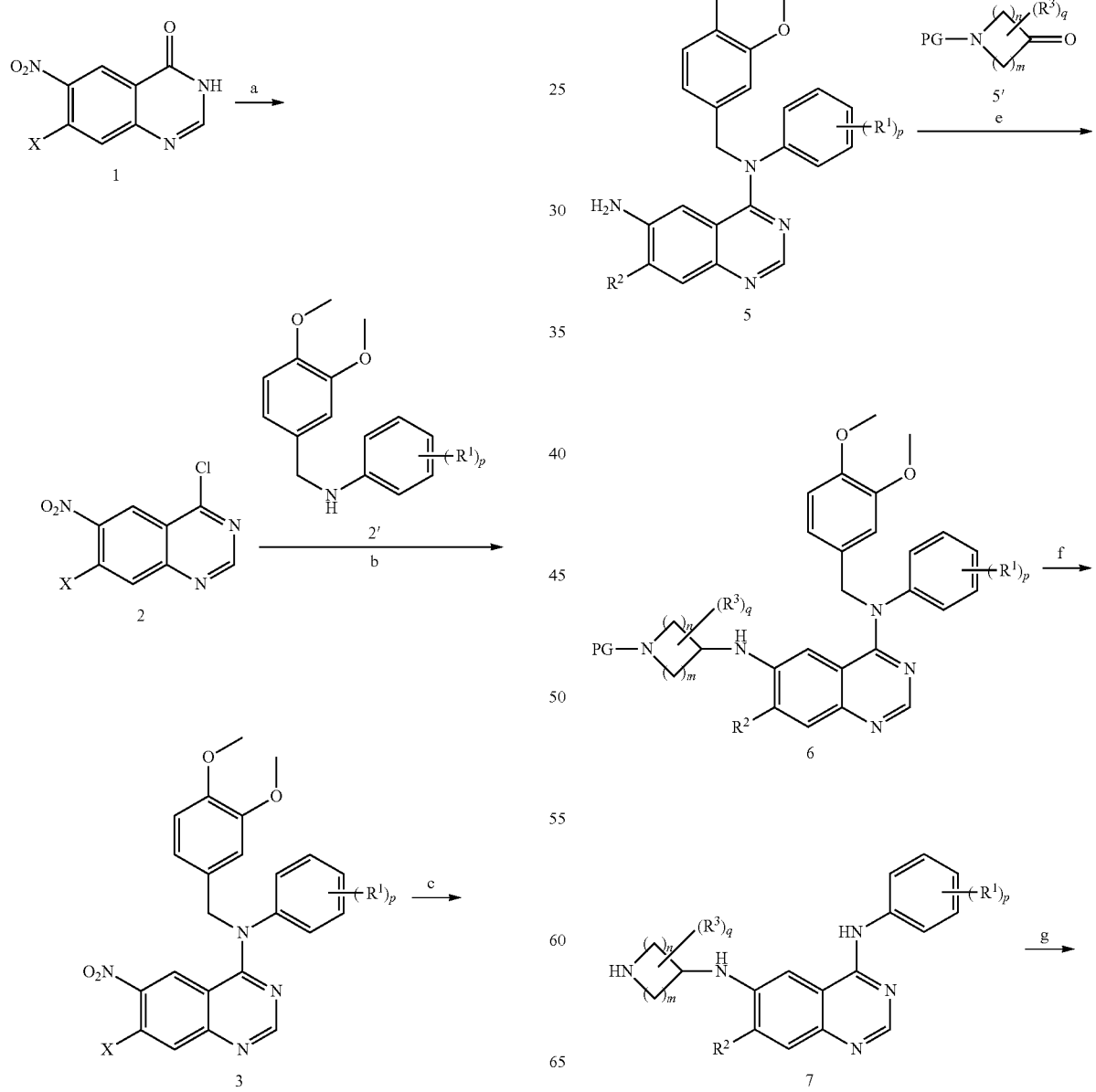

-continued

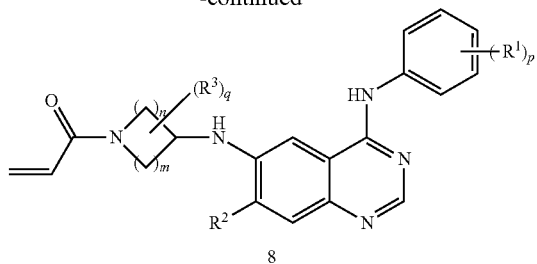

PG is an amino protecting group.

Under reflux condition, the compound of formula 1 reacts with thionyl chloride to form the compound of formula 2. The compound of formula 2 and the compound of 2' are refluxed in acetonitrile to obtain the compound of formula 3. The compound of formula 3 reacts with $R^2H$ in the presence of potassium tert-butoxide and DMSO to form the compound of formula 4. The compound of formula 4 is reduced with hydrogen in the presence of Raney nickel to obtain the compound of formula 5. In the presence of trifluoroacetic acid or acetic acid, and sodium triacetoxyborohydride, the compound of formula 5 reacts with the compound of formula 5' to form the compound of formula 6. The compound of formula 6, heated to 60° C. in the presence of trifluoroacetic acid, or in the hydrochloric acid-methanol solution, forms the compound of formula 7. In the presence of diisopropylethylamine and tetrahydrofuran, the compound of formula 7 reacts with acryloyl chloride to form the compound of formula 8.

Scheme 2:

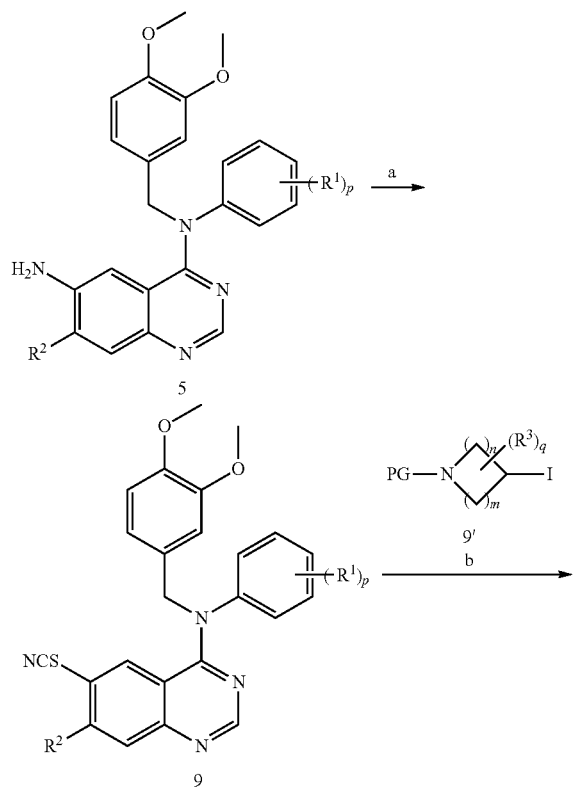

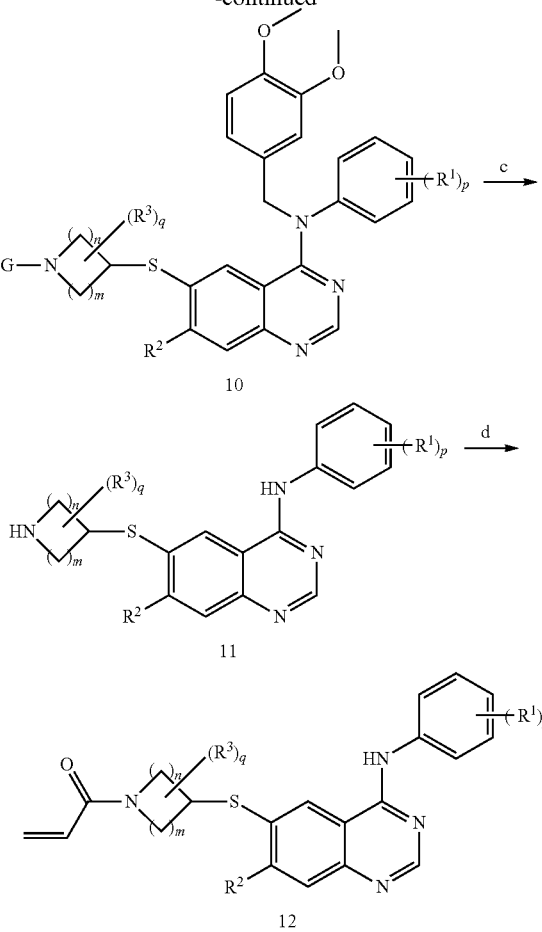

In the presence of sodium nitrite, sulfuric acid, potassium thiocyanate, ferric chloride and $H_2O$, the compound of formula 5 reacts and forms the compound of formula 9. In the presence of sodium borohydride, potassium carbonate and ethanol, the compound of formula 9 reacts with the compound of formula 9' to form the compound of formula 10. The compound of formula 10 is heated to 60° C. in the presence of trifluoroacetic acid to form the compound of formula 11. The compound of formula 11 reacts with acryloyl chloride to form the compound of formula 12.

The schemes above only list the methods for preparing part of the compounds of the present disclosure. According to the well-known techniques in this field, based on the schemes shown above, those skilled in the art may synthesize the compounds of the present disclosure with similar methods.

The compounds of the present disclosure may be asymmetric, e.g., with one or more stereoisomers. Unless otherwise specified, all the stereoisomers include e.g., enantiomers and diastereomers. The compounds with asymmetric carbon atoms of the disclosure can be isolated in optically active pure form or racemic form. The optically active pure form can be resolved from racemic mixture, or synthesized through chiral materials or chiral reagents.

The pharmaceutically acceptable salts of the compound of formula (I) of the present disclosure, formed with inorganic acid or organic acid, can also be used. Said organic acid or inorganic acid are, for example, hydrochloric acid, hydrobromic acid, sulfuric acid, phosphoric acid, nitric acid, acetic acid, lactic acid, malonic acid, succinic acid, fumaric acid, malic acid, mandelic acid, tartaric acid, citric acid, ascorbic acid, palmitic acid, maleic acid, benzoic acid, phenylacetic acid, cinnamic acid, salicylic acid, methanesulfonic acid, benzenesulfonic acid, methylbenzenesulfonic acid.

Another aspect of the present disclosure further relates to a pharmaceutical composition, which comprises the compound of formula I as defined by the present disclosure or the pharmaceutical acceptable salts thereof, and pharmaceutical acceptable carriers.

The pharmaceutical composition of the present disclosure can be prepared through combining the compounds of the present disclosure and suitable pharmaceutical acceptable carriers. For example, it can be prepared as solid, semi-solid, liquid or gaseous formulations, such as tablets, pills, capsules, powder, granules, ointments, emulsions, suspensions, solutions, suppositories, injections, inhalants, gels, microspheres and aerosol, etc.

The typical routes for the administration of the compounds of the present disclosure or the pharmaceutically acceptable salts thereof or the pharmaceutical composition thereof include, but are not limited to oral, rectal, transmucosal, enteral administration, or topical, percutaneous, inhalational, parenteral, sublingual, intravaginal, intranasal, intraocular, intraperitoneal, intramuscular, subcutaneous, intravenous administration. The preferred administration route is oral administration.

The pharmaceutical composition of the present disclosure can be manufactured through the well-known methods in the art, such as the mix, dissolving, granulation, sugar coating, grinding, emulsification, freeze-drying, etc.

In a preferred embodiment, the pharmaceutical composition is in the form for oral use. For oral administration, the active compounds can be mixed with the pharmaceutically acceptable carriers known in the art, to prepare the pharmaceutical composition. With these carriers, the compounds of the present disclosure can be formulated into tablets, pills, lozenges, sugar-coated tablets, capsules, liquid, gels, syrup, suspensions and the like, for oral administration to the patients.

The solid oral use composition can be prepared through conventional mixing, filling or compressing methods. For example, it can be obtained through the following method: the active compounds are mixed with the solid excipients; optionally the resulting mixture is ground, and other suitable adjuvants are added if necessary; then the mixture is processed into granules, so that the core of the tablets or sugar-coated tablets is obtained. Suitable adjuvants include, but are not limited to, adhesives, diluents, disintegrants, lubricants, glidants, sweeteners or flavoring agents, etc., such as microcrystalline cellulose, glucose solution, mucilage of gum arabic, gelatin solution, sucrose and starch paste; talc, starch, magnesium stearate, calcium stearate or stearic acid; lactose, sucrose, starch, mannitol, sorbitol or dicalcium phosphate; silica; crosslinked sodium carboxymethylcellulose, pre-gelatinized starch, sodium starch glycolate, alginic acid, corn starch, potato starch, methyl cellulose, agar, carboxymethyl cellulose, crosslinked polyvinylpyrrolidone, etc. Optionally, the core of the tablet can be coated through the well-known methods in general pharmaceutical practice, and enteric coating is particularly used.

The pharmaceutical composition is also suitable for parenteral administration, such as sterile solutions, suspensions or freeze-dried products in adequate unit dose form. The suitable excipients, such as fillers, buffers or surfactants, can also be used.

Another aspect of the present disclosure relates to the use of the compound of formula I of the present disclosure, or the pharmaceutically acceptable salts thereof, or the pharmaceutical composition thereof, for the manufacture of a medicament for prevention or treatment of tumor.

In all the methods for applying the compound of general formula I according to the disclosure, the daily administered dosage is preferably 0.01~200 mg/kg body weight.

Unless otherwise defined, all the technical and scientific terms used herein have the same meaning as commonly understood by a person skilled in the field that the claimed subject matters belong to. Unless otherwise specified, all the patents, patent applications and publications are incorporated herein in their entireties by reference.

It should also be noted that, unless otherwise specified, the expression "or" means "and/or". Furthermore, the term "include" and other forms such as "comprise", "contain" and "have" as used herein are not restrictive.

Unless otherwise specified, the terms used herein have the following meanings:

The term "halogen" refers to fluorine, chlorine, bromine or iodine, preferably fluorine or chlorine.

The term "hydroxy group" refers to —OH.

The term "mercapto group" refers to —SH.

The term "cyano group" refers to —CN.

The term "nitro group" refers to —$NO_2$.

The term "alkyl group" refers to a linear or branched saturated aliphatic hydrocarbon group consists of carbon atoms and hydrogen atoms, which links to the rest of the molecule through a single bond. For example, the alkyl group may have 1-6 carbon atoms (represented by $C_{1-6}$ alkyl group), and preferably have 1-4 carbon atoms. The non-limiting examples of alkyl group include, but are not limited to, methyl, ethyl, propyl, 2-propyl, n-butyl, isobutyl, t-butyl, n-pentyl, 2-methylbutyl, neopentyl, n-hexyl.

The term "alkoxy group" refers to —O— alkyl group, wherein the alkyl group is the same as defined above. The alkoxy group may have 1-6 carbon atoms, preferably 1-4 carbon atoms. The non-limiting examples of alkoxy group include, but are not limited to, methoxy, ethoxy, propoxy, isopropoxy, n-butoxy, isobutoxy, t-butoxy, n-pentyloxy, 2-methylbutoxy, neopentyloxy, n-hexoxy.

The term "alkylthio group" refers to —S-alkyl group, wherein the alkyl group is the same as defined above.

The term "amino group" refers to —$NH_2$.

The term "mono(alkyl) amino group" refers to —NH (alkyl group), wherein the alkyl group is the same as defined above.

The term "di(alkyl) amino group" refers to —N(alkyl group)$_2$, wherein the alkyl group is the same as defined above, and the two alkyl groups can be the same or different.

The term "cycloalkyl group" refers to saturated or unsaturated non-aromatic cyclic hydrocarbon group. The non-limiting examples of cycloalkyl group include, but are not limited to, cyclopropyl, cyclobutyl, cyclopentyl, cyclohexyl, cycloheptyl, etc.

The term "alkenyl group" refers to a linear or branched alkenyl group, preferably a linear or branched alkenyl group which has 2-6 carbon atoms. The non-limiting examples of alkenyl group include, but are not limited to, vinyl, 1-propenyl, 2-propenyl, 1-butenyl, isobutenyl.

The term "alkynyl group" refers to a linear or branched alkynyl group, preferably a linear or branched alkynyl group which has 2-6 carbon atoms. The non-limiting examples of alkynyl group include, but are not limited to ethynyl, 1-propynyl, 2-propynyl.

The term "aryl group" refers to an all-carbon monocyclic or fused polycyclic aromatic ring group which has conjugated π-electron system. It preferably has 6-14 carbon atoms, more preferably has 6-12 carbon atoms, most preferably has 6 carbon atoms. The non-limiting examples of aryl group include, but are not limited to, phenyl, naphthyl and anthracyl.

The term "heteroaryl group" refers to a monocyclic or fused ring which has 5, 6, 7, 8, 9, 10, 11 or 12 ring atoms, wherein the ring has 1, 2, 3 or 4 ring atoms selected from N, O, S, while the rest ring atoms are C, and the ring has a completely conjugated π-electron system. The heteroaryl group preferably has a 5- or 6-membered ring, more preferably a 5-membered ring. The non-limiting examples of heteroaryl group include, but are not limited to pyrrolyl, furanyl, thienyl, imidazolyl, oxazolyl, pyrazolyl, pyridyl, pyrimidinyl, pyrazinyl, quinolyl, isoquinolyl, tetrazolyl, triazolyl, triazinyl.

The term "heterocycloalkyl group" refers to a monocyclic or fused ring which has 3, 4, 5, 6, 7, 8, 9, 10, 11 or 12 ring atoms, wherein 1, 2 or 3 ring atoms are heteroatoms selected from N, O, $S(O)_n$ (where n is 0, 1 or 2), while the rest ring atoms are C. Such a ring may be saturated or unsaturated (for example with one or more double bonds), but lack completely conjugated n-electron system. The examples of 3-membered heterocycloalkyl group include, but are not limited to oxiranyl, thiiranyl, aziridinyl. The examples of 4-membered heterocycloalkyl group include, but are not limited to azetidinyl, oxetanyl, thietanyl. The examples of 5-membered heterocycloalkyl group include, but are not limited to tetrahydrofuranyl, tetrahydrothienyl, pyrrolidinyl, isoxazolidinyl, oxazolidinyl, isothiazolidinyl, 1,1-dioxoisothiazolidinyl, thiazolidinyl, imidazolidinyl, tetrahydropyrazolyl, pyrrolinyl, dihydrofuranyl, dihydrothienyl. The examples of 6-membered heterocycloalkyl group include, but are not limited to piperidinyl, tetrahydropyranyl, tetrahydrothiopyranyl, morpholinyl, piperazinyl, 1,4-thioxanyl, 1,4-dioxanyl, thiomorpholinyl, 1,2- or 1,4-dithianyl, dihydropyridyl, tetrahydropyridyl, dihydropyranyl, tetrahydropyranyl, dihydrothiopyranyl. The examples of 7-membered heterocycloalkyl group include, but are not limited to azepanyl, oxepanyl, thiepanyl. A monocyclic heterocycloalkyl group which has 5 or 6 ring atoms is preferred.

The term "therapeutically effective amount" means that, when administered to mammals, preferably to humans, the compound of the present disclosure may be sufficient to effectively treat the diseases of the mammals (preferably humans). The amount of the compound of the present disclosure, which constitutes "therapeutically effective amount", varies depending on the nature of the compound, the state and severity of the disease, the route of administration and the age of the mammal to be treated. However the amount can be routinely determined by a person skilled in the art, based on his knowledge and the content of the present disclosure.

The term "treatment" means that the compound or formulation of the present disclosure is administrated, to prevent, alleviate or eliminate the disease, or one or more symptoms related to said disease. And it comprises:
  (i) to prevent the occurrence of the disease or morbid condition in mammals, particularly when such mammals are susceptible to the morbid condition, but have not yet been diagnosed as suffering from said morbid condition;
  (ii) to inhibit the disease or morbid condition, i.e., to suppress the development of the disease or morbid condition;
  (iii) to alleviate the disease or morbid condition, i.e., to promote the regression of the disease or morbid condition.

The term "pharmaceutical composition" refers to a formulation, which comprises one or more compounds of the present disclosure, or the salts thereof, along with the carriers, excipients and/or media generally accepted in the field for delivering the biologically active compounds to the organisms (such as humans). The purpose of pharmaceutical composition is to facilitate the administration of the compound of the present disclosure to the organisms.

The term "pharmaceutically acceptable carrier" refers to those carriers and diluents which have no significant irritation effect on the organisms, and do not impair the biological activity and performance of the active compounds. The "pharmaceutically acceptable carriers" include, but are not limited to, any carriers, excipients, media, glidants, sweeteners, diluents, preservatives, dyes/coloring agents, flavoring enhancers, surfactants, moistening agents, dispersants, disintegrants, suspending agents, stabilizers, isotonic agents, solvents or emulsifying agents, permitted by the Food and Drug Administration as acceptable to be applied to human or livestock animals.

EXPERIMENTS

All the manipulations of the moisture- and/or oxygen-sensitive experiments were performed under nitrogen atmosphere in pre-dried glassware. Unless otherwise specified, all the raw materials were commercially available materials, and they were not further purified before use.

For column chromatography, silica gel (200-300 mesh) manufactured by Qingdao Marine Chemical Research Institute was used. For thin layer chromatography (TLC), pre-coated chromatography plate (silica gel 60PF254, 0.25 mm) manufactured by E. Merck corp. was used.

The instrument used in nuclear magnetic resonance (NMR) spectral analysis was Varian VNMRS-400 resonance spectrometer. Chemical shift was referenced against the internal standard, tetramethylsilane (TMS=δ 0.00). The data of H-NMR spectrum were recorded as the following format: number of protons, peak pattern (s, singlet; d, doublet; t, triplet; q, quartet; m, multiplet), coupling constant (in terms of Hz).

For liquid chromatography-mass spectrometry, Agilent LC 1200 series (5 μm, C18 chromatography column) instrument was used.

Example 1 Synthesis of $N^6$-(1-acryloylazetidin-3-yl)-$N^4$-(3-chloro-4-fluorophenyl)-7-methoxyquinazoline-4,6-diamine (Compound E1)

Step 1: 4-chloro-7-fluoro-6-nitroquinazoline 7-fluoro-6-nitroquinazoline-4(3H)-one (2.0 g, 9.6 mmol) and a drop of N,N-dimethylformamide were refluxed overnight in thionyl chloride (6 mL) and concentrated in vacuo. After adding toluene, the solution was again concentrated in vacuo so that the excess thionyl chloride was removed, and the compound shown in the title (2 g, 92%) was obtained.

$^1$H NMR (CDCl$_3$): δ 9.18 (1H, s), 9.05 (1H, d, J=7.6 Hz), 7.95 (1H, d, J=10.4).

Step 2: 3-chloro-N-(3,4-dimethoxybenzyl)-4-fluoroaniline 3-chloro-4-fluoroaniline (2.9 g, 20 mmol) and 3,4-dimethoxybenzaldehyde (3.3 g, 20 mmol) were added into 1,2- dichloroethane (30 mL), stirred at room temperature for 1 h. Then sodium triacetoborohydride (10 g, 50 mmol) was added, and the reaction mixture was stirred at room temperature overnight. The reaction mixture was poured into 100 mL H$_2$O, extracted with dichloromethane. The organic phase was separated and washed with saturated brine, dried, concentrated in vacuo, and the compound shown in the title (5.5 g, 93%) was obtained.

$^1$H NMR (CDCl$_3$): δ 6.94-6.82 (4H, m), 6.63-6.61 (1H, m), 6.45-6.41 (1H, m), 4.18 (2H, s), 3.98 (1H, br), 3.87 (3H, s), 3.86 (3H, s).

Step 3: N-(3-chloro-4-fluorophenyl)-N-(3,4-dimethoxybenzyl)-7-fluoro-6-nitroquinazoline-4-amine 4-chloro-7-fluoro-6-nitroquinazoline (2.1 g, 9.2 mmol) and 3-chloro-N-(3,4-dimethoxybenzyl)-4-fluoroaniline (2.7 g, 9.2 mmol) were added into acetonitrile (20 mL), refluxed for 3 h. After cooling, sodium carbonate solution was added for neutralization. The mixture was extracted with ethyl acetate, and the organic phase was separated, washed with saturated brine, dried, concentrated in vacuo, and the compound shown in the title (3.6 g, 80%) was obtained.

Step 4: N-(3-chloro-4-fluorophenyl)-N-(3,4-dimethoxybenzyl)-7-methoxy-6-nitroquinazoline-4-amine Metallic sodium (113 mg, 5.0 mmol) was added into anhydrous methanol (20 mL), stirred at room temperature for 10 min. Then N-(3-chloro-4-fluorophenyl)-N-(3,4-dimethoxybenzyl)-7-fluoro-6-nitroquinazoline-4-amine (2.4 g, 5.0 mmol) was added. The reaction mixture was stirred at 40° C. for 6 h. After cooling, the reaction mixture was poured into 100 mL H$_2$O, extracted with ethyl acetate. The organic phase was washed with saturated brine, dried, concentrated in vacuo, and the compound shown in the title (2.35 g, 94%) was obtained.

$^1$H NMR (CDCl$_3$): δ 8.85 (1H, s), 7.57 (1H, s), 7.35 (1H, s), 7.23-7.19 (2H, m), 7.00-6.96 (1H, m), 6.84-6.78 (2H, m), 5.35 (2H, s), 4.05 (3H, s), 3.88 (3H, s), 3.83 (3H, s).

Step 5: N$^4$-(3-chloro-4-fluorophenyl)-N$^4$-(3,4-dimethoxybenzyl)-7-methoxyquinazoline-4,6-diamine N-(3-chloro-4-fluorophenyl)-N-(3,4-dimethoxybenzyl)-7-methoxy-6-nitroquinazoline-4-amine (2.35 g, 4.7 mmol) and about 0.5 g of Raney nickel were added into tetrahydrofuran (100 mL), replaced with hydrogen gas, stirred under hydrogen gas atmosphere (1 atm) overnight at room temperature. The mixture was filtered; the filtrate was concentrated in vacuo, and the compound shown in the title (2 g, 90%) was obtained.

$^1$H NMR (CDCl$_3$): δ 8.72 (1H, s), 7.17 (1H, s), 7.09-7.06 (1H, m), 7.00-6.95 (2H, m), 6.86-6.83 (1H, m), 6.79-6.74 (2H, m), 6.33 (1H, s), 5.30 (2H, s), 3.98-3.97 (5H, m), 3.83 (3H, s), 3.78 (3H, s).

Step 6: Benzyl 3-{{14-[(3-chloro-4-fluorophenyl)(3,4-dimethoxybenzyl)amino]-7-methoxyquinazoline-6-yl}amino}azetidine-1-carboxylate A solution of N$^4$-(3-chloro-4-fluorophenyl)-N$^4$-(3,4-dimethoxybenzyl)-7-methoxyquinazoline-4,6-diamine (1.10 g, 2.35 mmol) and benzyl 3-oxoazetidine-1-carboxylate (0.58 g, 2.83 mmol) in trifluoroacetic acid (7 mL) was stirred at room temperature for 10 min, then sodium triacetoborohydride (0.52 g, 2.45 mmol) was added all at once. After 0.5 h of reaction, additional benzyl 3-oxoazetidine-1-carboxylate (0.24 g, 1.17 mmol) and sodium triacetoborohydride (0.25 g, 1.17 mmol) were added, and the reaction was allowed to proceed for another 0.5 h. Once the reaction was complete, H$_2$O was added slowly to quench the reaction, and the solution was extracted with ethyl acetate. The resulting organic phase was sequentially washed with H$_2$O, 5% NaHCO$_3$ solution and saturated brine, dried over anhydrous sodium sulfate and concentrated in vacuo. The residue was made into slurry with ethyl ether, filtered, and the compound shown in the title (1.3 g, 84%) was obtained.

$^1$H NMR (CDCl$_3$): δ 8.79 (1H, s), 7.68 (1H, br), 7.31-7.37 (5H, m), 7.05-7.11 (2H, m), 6.86-6.88 (2H, m), 6.79-6.82 (1H, m), 6.73-6.75 (1H, m), 5.77 (1H, s), 5.32 (2H, s), 5.10 (2H, s), 4.83 (1H, d, J=5.6 Hz), 3.83-3.97 (5H, m), 3.83 (3H, s), 3.77 (3H, s), 3.55-3.62 (3H, m).

Step 7: N$^6$-(azetidin-3-yl)-N$^4$-(3-chloro-4-fluorophenyl)-7-methoxyquinazoline-4,6-diamine A solution of benzyl 3-{{14-[(3-chloro-4-fluorophenyl)(3,4-dimethoxybenzyl)amino]-7-methoxyquinazolin-6-yl}amino}azetidine-1-carboxylate (1.2 g, 1.82 mmol) in trifluoroacetic acid (8 mL) was stirred at 70° C. for 6 h. Once the reaction was complete, the reaction solution was cooled and concentrated in vacuo. The residue was made into slurry with ethyl acetate, filtered, and a trifluoroacetate salt of the compound shown in the title (0.74 g, 84%) was obtained.

$^1$H NMR (DMSO-d6): δ 10.50 (1H, s), 9.04 (1H, s), 8.80 (1H, s), 8.70 (1H, s), 7.95-7.98 (1H, m), 7.65-7.68 (1H, m), 7.52-7.57 (1H, m), 7.24 (1H, s), 7.14 (1H, s), 6.86-6.89 (1H, m), 4.50-4.56 (1H, m), 4.41-4.44 (2H, m), 4.04-4.11 (5H, m).

Step 8: N$^6$-(1-acryloylazetidin-3-yl)-N$^4$-(3-chloro-4-fluorophenyl)-7-methoxyquinazoline-4,6-diamine A suspension of trifluoroacetate salt of N$^6$-(azetidin-3-yl)-N$^4$-(3-chloro-4-fluorophenyl)-7-methoxyquinazoline-4,6-diamine (0.89 g, 1.82 mmol) and triethylamine (1 mL) in tetrahydrofuran (20 mL) was stirred at room temperature for 30 min, cooled to −40° C., and a solution of acryloyl chloride (166 mg, 1.82 mmol) in tetrahydrofuran (2 mL) was slowly added dropwise. The reaction was allowed to proceed for another 30 min. Once the reaction was complete, 5% NaHCO$_3$ solution was slowly added to quench the reaction, and the solution was extracted with ethyl acetate. The resulting organic phase was washed with saturated brine, dried over anhydrous sodium sulfate, and concentrated in vacuo. The residue was made into slurry with ethyl acetate, and the compound shown in the title (0.32 g, 41%) was obtained.

$^1$H NMR (CDCl$_3$): δ 8.59 (1H, s), 7.92 (1H, s), 7.83-7.85 (1H, m), 7.57-7.59 (1H, m), 7.19 (1H, s), 7.10-7.15 (1H, m), 6.68 (1H, s), 6.35-6.38 (1H, m), 6.17-6.31 (1H, m), 5.68-5.71 (1H, m), 5.05 (1H, d, J=6.4 Hz), 4.58-4.63 (2H, m), 4.42-4.48 (1H, m), 4.10-4.14 (1H, m), 4.01-4.03 (4H, m).

Example 2 Synthesis of N$^6$-(1-acryloylpiperidin-4-yl)-N$^4$-(3-chloro-4-fluorophenyl)-7-methoxyquinazoline-4,6-diamine (Compound E2)

Step 1: tert-butyl 4-{{4-[(3-chloro-4-fluorophenyl)(3,4-dimethoxybenzyl)amino]-7-methoxyquinazolin-6-yl}amino}piperidine-1-carboxylate A solution of N$^4$-(3-chloro-4-fluorophenyl)-N$^4$-(3,4-dimethoxybenzyl)-7-methoxyquinazoline-4,6-diamine (469 mg, 1.0 mmol) and tert-butyl 4-oxopiperidine-1-carboxylate (239 mg, 1.2 mmol) in acetic acid (10 mL) was stirred at room temperature for 2 h, then sodium triacetoxyborohydride (254 mg, 1.2 mmol) was added all at once. After 0.5 h of reaction, $H_2O$ was added slowly to quench the reaction. The solution was extracted with ethyl acetate. The resulting organic phase was sequentially washed with $H_2O$, 5% $NaHCO_3$ aqueous solution and saturated brine, dried over anhydrous sodium sulfate, and concentrated in vacuo. The residue was separated through silica column chromatography, and the compound shown in the title (404 mg, 62%) was obtained.

$^1$H NMR (DMSO-d6): δ 8.57 (1H, s), 7.33-7.27 (2H, m), 7.09 (1H, s), 6.99 (1H, m), 6.84-6.80 (1H, m), 6.81-6.80 (1H, m), 6.79-6.78 (1H, m), 5.99 (1H, m), 5.29 (2H, s), 3.91 (3H, m), 3.85-3.82 (2H, m), 3.64 (3H, m), 3.61 (3H, m), 2.80-2.75 (1H, m), 2.59-2.53 (2H, m), 1.42-1.37 (11H, m), 1.20-1.17 (2H, m).

Step 2: $N^6$-(piperidin-4-yl)-$N^4$-(3-chloro-4-fluorophenyl)-7-methoxyquinazoline-4,6-diamine With a method similar with that described in Step 7, Example 1, the compound shown in the title was synthesized from the product of Step 1.

$^1$HNMR (DMSO-d6): δ 10.62 (1H, s), 8.75 (1H, s), 8.68-8.60 (1H, br), 8.50-8.41 (1H, br), 7.96-7.94 (1H, m), 7.66-7.64 (1H, m), 7.58-7.56 (1H, m), 7.39 (1H, s), 7.20 (1H, s), 6.19-6.17 (1H, m), 4.05 (3H, s), 3.80-3.60 (2H, m), 3.05-2.96 (2H, m), 2.16-2.12 (2H, m), 1.78-1.74 (2H, m).

Step 3: $N^6$-(1-acryloylpiperidin-4-yl)-$N^4$-(3-chloro-4-fluorophenyl)-methoxyquinazoline-4,6-diamine A solution of mono trifluoroacetate salt of $N^6$-(piperidin-4-yl)-$N^4$-(3-chloro-4-fluorophenyl)-7-methoxyquinazoline-4,6-diamine (258 mg, 0.5 mmol) and triethylamine (202 mg, 2.0 mmol) in tetrahydrofuran (10 mL) was stirred at room temperature for 30 min. After cooled to 0° C., a solution of acryloyl chloride (54 mg, 0.6 mmol) in tetrahydrofuran (2 mL) was added dropwise, then the reaction was allowed to proceed for another 30 min. Once the reaction was complete, 5% $NaHCO_3$ solution was slowly added to quench the reaction. The solution was extracted with ethyl acetate. The resulting organic phase was washed with saturated brine, dried over anhydrous sodium sulfate, and concentrated in vacuo. The residue was separated through silica column chromatography, and the target product (150 mg, 66%) was obtained.

$^1$H NMR (DMSO-d6): δ 9.24 (1H, s), 8.33 (1H, s), 8.09-8.08 (1H, m), 7.77-7.74 (1H, m), 7.42-7.40 (1H, m), 7.23 (1H, s), 7.06 (1H, s), 6.85-6.81 (1H, m), 6.10-6.06 (1H, m), 5.66-5.64 (1H, m), 5.32-5.29 (1H, m), 4.41-4.38 (1H, m), 4.09-4.06 (1H, m), 3.93 (3H, s), 3.79-3.78 (1H, m), 3.35-3.34 (1H, m), 2.87-2.84 (1H, m), 2.03-2.01 (2H, m), 1.44-1.41 (2H, m).

Example 3 Synthesis of (S)—$N^6$-(1-acryloylazetidin-3-yl)-$N^4$-(3-chloro-4-fluorophenyl)-7-(tetrahydrofuran-3-yloxy)quinazoline-4,6-diamine (Compound E3)

Step 1: N-(3-chloro-4-fluorophenyl)-7-fluoro-6-nitroquinazoline-4-amine 4-chloro-7-fluoro-6-nitroquinazoline (2.28 g, 10 mmol) and 3-chloro-4-fluoroaniline (1.46 g, 10 mmol) were dissolved in acetonitrile (50 mL), refluxed under heating for 1 h. The solution was concentrated in vacuo and the solvent was removed. Saturated sodium carbonate and ethyl acetate were added into the residue. The solution was stirred for 10 min, then separated. The aqueous phase was extracted with ethyl acetate. The organic phases were combined, and dried over anhydrous sodium sulfate. The solution was concentrated in vacuo and the solvent was removed. The residue was made into slurry with diethyl ether, filtered, and the compound shown in the title (3.01 g, 90%) was obtained.

$^1$H NMR (DMSO-d6): δ 10.51 (1H, s), 9.58 (1H, d, J=8.0 Hz), 8.73 (1H, s), 8.13 (1H, dd, J=6.8 Hz, 2.8 Hz), 7.85 (1H, d, J=12.4 Hz), 7.77-7.61 (1H, m), 7.49 (1H, t, J=9.2 Hz).

Step 2: (S)—N-(3-chloro-4-fluorophenyl)-7-(tetrahydrofuran-3-yloxy)-6-nitroquinazoline-4-amine N-(3-chloro-4-fluorophenyl)-7-fluoro-6-nitroquinazoline-4-amine (37.1 g, 0.11 mol) and (S)-3-hydroxytetrahydrofuran (13.6 g, 0.154 mol) were dissolved in dried DMSO (200 mL). Potassium tert-butoxide (30.9 g, 0.275 mol) was added in batches; meanwhile the internal temperature was kept at 30° C. or lower by a water bath. The solution was stirred at room temperature for 4 h. The reaction mixture was poured into 1.2 L of $H_2O$, filtered with suction, washed with $H_2O$ and dried to obtain the crude product. The crude product was then made into slurry with ethanol, filtered off with suction, to obtain the compound shown in the title (33.4 g, 75%).

$^1$H NMR (DMSO-d6): δ 10.08 (1H, s), 9.15 (1H, s), 8.61 (1H, s), 8.11-8.09 (1H, m), 7.77-7.74 (1H, m), 7.43-7.39 (2H, m), 5.41-5.38 (1H, m), 3.96-3.92 (1H, m), 3.87-3.73 (3H, m), 2.33-2.28 (1H, m), 2.06-2.01 (1H, m).

Step 3: (S)—$N^4$-(3-chloro-4-fluorophenyl)-7-(tetrahydrofuran-3-yloxy)quinazoline-4,6-diamine With a method similar with that described in Step 5, Example 1, the compound shown in the title was synthesized from (S)—N-(3-chloro-4-fluorophenyl)-7-(tetrahydrofuran-3-yloxy)-6-nitroquinazoline-4-amine.

$^1$H NMR (DMSO-d6): δ 8.55 (1H, s), 7.96-7.93 (1H, m), 7.56-7.51 (1H, m), 7.18-7.13 (3H, m), 6.97 (1H, s), 5.13-5.10 (1H, m), 4.30 (1H, br), 4.13-4.03 (3H, m), 3.96-3.91 (1H, m), 2.39-2.34 (1H, m), 2.26-2.22 (1H, m).

Step 4: benzyl (S)-3-{{4-[(3-chloro-4-fluorophenyl)amino]-7-(tetrahydrofuran-3-yloxy)quinazolin-6-yl}amino}azetidine-1-carboxylate With a method similar with that described in Step 6, Example 1, the compound shown in the title was synthesized from (S)—$N^4$-(3-chloro-4-fluorophenyl)-7-(tetrahydrofuran-3-yloxy) quinazoline-4,6-diamine.

$^1$H NMR (CDCl$_3$): δ 10.63 (1H, br), 8.08-8.10 (1H, m), 8.02 (1H, s), 7.69-7.73 (1H, m), 7.31-7.37 (5H, m), 7.15-7.19 (1H, m), 7.00 (1H, s), 6.76 (1H, s), 5.12 (2H, s), 5.03-5.05 (1H, m), 4.52-4.60 (3H, m), 4.30-4.35 (1H, m), 3.91-4.00 (2H, m), 3.74-3.85 (4H, m), 2.14-2.20 (1H, m), 1.95-2.00 (1H, m).

Step 5: (S)—$N^6$-(azetidin-3-yl)-$N^4$-(3-chloro-4-fluorophenyl)-7-(tetrahydrofuran-3-yloxy)quinazoline-4,6-diamine With a method similar with that described in Step 7, Example 1, a trifluoroacetate salt of the compound shown in the title was synthesized from benzyl (S)-3-{{4-[(3-chloro-4-fluoro phenyl) amino]-7-(tetrahydrofuran-3-yloxy)quinazolin-6-yl}amino}azetidine-1-carboxylate.

$^1$H NMR (DMSO-d6): δ 10.80 (1H, s), 9.10 (1H, br), 8.90 (1H, br), 8.69 (1H, s), 7.90-7.93 (1H, m), 7.60-7.63 (1H, m), 7.50-7.574 (1H, m), 7.23 (1H, s), 7.11 (1H, s), 6.68 (1H, d, J=5.6 Hz), 5.22-2.24 (1H, m), 4.40-4.5 (3H, m), 3.90-4.09 (5H, m), 3.76-3.81 (1H, m), 2.43-2.48 (1H, m), 2.14-2.18 (1H, m).

Step 6: (S)—$N^6$-(1-acryloylazetidin-3-yl)-$N^4$-(3-chloro-4-fluorophenyl)-7-(tetrahydrofuran-3-yloxy) quinazoline-4,6-diamine With a method similar with that described in Step 8, Example 1, the compound shown in the title was synthesized from the trifluoroacetate salt of (S)—$N^6$-(azetidin-3-yl)-$N^4$-(3-chloro-4-fluorophenyl)-7-(tetrahydrofuran-3-yloxy)quinazoline-4,6-diamine.

$^1$H NMR (CDCl$_3$): δ 8.59 (1H, s), 7.97 (1H, s), 7.85-7.87 (1H, m), 7.56-7.59 (1H, m), 7.10-7.15 (2H, m), 6.70 (1H, s), 6.30-6.35 (1H, m), 6.19-6.26 (1H, m), 5.68-5.71 (1H, m), 5.13 (1H, s), 5.01 (1H, d, J=6.4 Hz), 4.60-4.63 (2H, m), 4.42-4.46 (1H, m), 4.01-4.19 (5H, m), 3.91-3.94 (1H, m), 2.35-2.41 (1H, m), 2.22-2.29 (1H, m).

Example 4 Synthesis of (S)—$N^6$-(1-acryloylpiperidin-4-yl)-$N^4$-(3-chloro-4-fluorophenyl)-7-(tetrahydrofuran-3-yloxy)quinazoline-4,6-diamine (Compound E4)

Step 1: tert-butyl (S)-4-(4-(3-chloro-4-fluorophenylamino)-7-(tetrahydrofuran-3-yloxy)quinazolin-6-ylamino)piperidine-1-carboxylate With a method similar with that described in Step 1, Example 2, the compound shown in the title was synthesized from (S)—$N^4$-(3-chloro-4-fluorophenyl)-7-(tetrahydrofuran-3-yloxy)quinazoline-4,6-diamine $^1$H NMR (CDCl$_3$): δ 8.53 (1H, s), 7.84-7.82 (1H, m), 7.54-7.50 (1H, m), 7.18-7.10 (3H, m), 6.62 (1H, s), 5.10-5.09 (1H, m), 4.62 (1H, d, J=8.0 Hz), 4.10-3.88 (6H, m), 3.61-3.57 (1H, m), 3.05-2.98 (2H, m), 2.38-2.07 (4H, m), 1.53-1.43 (11H, m).

Step 2: (S)—$N^6$-(piperidin-4-yl)-$N^4$-(3-chloro-4-fluorophenyl)-7-(tetrahydrofuran-3-yloxy)quinazoline-4,6-diamine tert-butyl (S)-4-(4-(3-chloro-4-fluorophenylamino)-7-(tetrahydrofuran-3-yloxy)quinazolin-6-ylamino)piperidin-1-carboxylate (1.0 g, 1.79 mmol) was added into a 1 mol/L solution of HCl in methanol (10 mL), stirred at room temperature overnight. The solution was concentrated in vacuo, and sodium bicarbonate solution was added, then stirred for 1 h. The solution was extracted with a mixed solution of ethyl acetate and methanol. The organic phase was dried and concentrated in vacuo, and the compound shown in the title (500 mg, 61%) was obtained.

Step 3: (S)—$N^6$-(1-acryloylpiperidin-4-yl)-$N^4$-(3-chloro-4-fluorophenyl)-7-(tetrahydrofuran-3-yloxy) quinazoline-4,6-diamine With a method similar with that described in Step 3, Example 2, the compound shown in the title was synthesized from (S)—$N^6$-(piperidin-4-yl)-$N^4$-(3-chloro-4-fluorophenyl)-7-(tetrahydrofuran-3-yloxy)quinazoline-4,6-diamine.

$^1$H NMR (CDCl$_3$): δ 8.40 (1H, s), 7.74-7.71 (1H, m), 7.49-7.45 (1H, m), 7.07-7.03 (2H, m), 6.76 (1H, s), 6.56-6.49 (1H, m), 6.25-6.20 (1H, m), 5.66-5.63 (1H, m), 5.01-4.98 (1H, m), 4.55-4.41 (2H, m), 4.00-3.65 (6H, m), 3.28-3.21 (1H, m), 3.00-2.89 (1H, m), 1.53-1.43 (2H, m).

Example 5 Synthesis of (S)—$N^6$-(1-acryloylpiperidin-3-yl)-$N^4$-(3-chloro-4-fluorophenyl)-7-(tetrahydrofuran-3-yloxy)quinazoline-4,6-diamine (Compound E5)

Step 1: tert-butyl (S)-3-(4-(3-chloro-4-fluorophenylamino)-7-(tetrahydrofuran-3-yloxy)quinazolin-6-ylamino)piperidine-1-carboxylate With a method similar with that described in Step 1, Example 2, the compound shown in the title was synthesized from (S)—$N^4$-(3-chloro-4-fluorophenyl)-7-(tetrahydrofuran-3-yloxy)quinazoline-4,6-diamine and tert-butyl 3-oxopiperidine-1-carboxylate.

$^1$H NMR (CDCl$_3$): δ 8.56 (1H, s), 8.26-8.37 (1H, brs), 8.03-8.05 (1H, m), 7.90-7.94 (1H, m), 7.41 (1H, s), 7.12 (1H, t, J=8.8 Hz), 6.98 (1H, s), 5.14 (1H, s), 5.02 (1H, s), 4.56-4.60 (1H, m), 3.93-4.06 (4H, m), 3.80-3.90 (2H, m), 3.26-3.33 (1H, m), 2.87-2.94 (1H, m), 2.37-2.47 (1H, m), 2.27-2.32 (1H, m), 2.17-2.22 (2H, m), 1.65-1.75 (2H, m), 1.43 (9H, s).

Step 2: (S)—$N^6$-(piperidin-3-yl)-$N^4$-(3-chloro-4-fluorophenyl)-7-(tetrahydrofuran-3-yloxy)quinazoline-4,6-diamine With a method similar with that described in Step 2, Example 4, the compound shown in the title was synthesized from tert-butyl (S)-3-(4-(3-chloro-4-fluorophenylamino)-7-(tetrahydrofuran-3-yloxy)quinazolin-6-ylamino)piperidine-1-carboxylate.

Step 3: (S)—$N^6$-(1-acryloylpiperidin-3-yl)-$N^4$-(3-chloro-4-fluorophenyl)-7-(tetrahydrofuran-3-yloxy) quinazoline-4,6-diamine With a method similar with that described in Step 3, Example 2, the compound shown in the title was synthesized from (S)—$N^6$-(piperidin-3-yl)-$N^4$-(3-chloro-4-fluorophenyl)-7-(tetrahydrofuran-3-yloxy)quinazoline-4,6-diamine.

$^1$H NMR (CDCl$_3$): δ 8.89-9.07 (1H, brs), 8.64 (1H, s), 8.35-8.39 (1H, m), 8.21-8.27 (1H, m), 7.76-7.86 (1H, m), 7.16-7.22 (2H, m), 6.71 (1H, dd, J=17.2 Hz, 10.4 Hz), 6.54 (1H, dd, J=47.2 Hz, 1.2 Hz), 5.89 (1H, dd, J=10.8 Hz, 1.2 Hz), 5.23-5.29 (2H, m), 4.66-4.74 (1H, m), 4.05-4.19 (4H, m), 3.87-3.97 (1H, m), 3.26-3.43 (3H, m), 2.46-2.60 (1H, m), 2.21-2.35 (1H, m), 2.01-2.10 (2H, m), 1.64-1.78 (2H, m).

Example 6 Synthesis of (S)—$N^6$-(1-acryloylpyrrolidin-3-yl)-$N^4$-(3-chloro-4-fluorophenyl)-7-(tetrahydrofuran-3-yloxy)quinazoline-4,6-diamine (Compound E6)

Step 1: tert-butyl (S)-3-(4-(3-chloro-4-fluorophenylamino)-7-(tetrahydrofuran-3-yloxy)quinazolin-6-ylamino)pyrrolidine-1-carboxylate With a method similar with that described in Step 1, Example 2, the compound shown in the title was synthesized from (S)—N⁴-(3-chloro-4-fluorophenyl)-7-(tetrahydrofuran-3-yloxy)quinazoline-4,6-diamine and tert-butyl 3-oxopyrrolidine-1-carboxylate.

Step 2: (S)—N⁶-(pyrrolidin-3-yl)-N⁴-(3-chloro-4-fluorophenyl)-7-(tetrahydrofuran-3-yloxy)quinazoline-4,6-diamine With a method similar with that described in Step 2, Example 4, the compound shown in the title was synthesized from tert-butyl (S)-3-(4-(3-chloro-4-fluorophenylamino)-7-(tetrahydrofuran-3-yloxy)quinazolin-6-ylamino)pyrrolidine-1-carboxylate.

Step 3: (S)—N⁶-(1-acryloylpyrrolidin-3-yl)-N⁴-(3-chloro-4-fluorophenyl)-7-(tetrahydrofuran-3-yloxy)quinazoline-4,6-diamine With a method similar with that described in Step 3, Example 2, the compound shown in the title was synthesized from (S)—N⁶-(pyrrolidin-3-yl)-N⁴-(3-chloro-4-fluorophenyl)-7-(tetrahydrofuran-3-yloxy)quinazoline-4,6-diamine.
¹H NMR (CDCl₃): δ 8.97-8.57 (1H, m), 8.54-8.48 (1H, m), 7.84-7.76 (1H, m), 7.66-7.62 (1H, m), 7.40-7.20 (1H, m), 7.11-6.98 (2H, m), 6.49-6.32 (2H, s), 5.74-5.67 (1H, s), 5.10-5.09 (1H, s), 4.66-4.63 (1H, m), 4.30-3.20 (8H, m), 2.42-1.91 (3H, m), 1.43-1.42 (1H, m).

Example 7 Synthesis of 1-(4-(4-(3-chloro-4-(3-fluorobenzyloxy)phenylamino)-7-methoxyquinazoline-6-ylamino)piperidin-1-yl)prop-2-ene-1-one (Compound E7)

Step 1: 2-chloro-1-(3-fluorobenzyloxy)-4-nitrobenzene 2-chloro-4-nitrophenol (3.4 g, 20 mmol), 3-fluorobenzyl chloride (2.8 g, 20 mmol) and potassium carbonate (3.3 g, 24 mmol) was refluxed in acetonitrile (30 mL) overnight. The reaction mixture was poured into 100 mL of H₂O, extracted with ethyl acetate. The organic phase was washed with saturated brine, dried, concentrated in vacuo to obtain the crude product. The crude product was washed with petroleum ether, filtered and dried, and the compound shown in the title (3.2 g, 57%) was obtained.
¹H NMR (CDCl₃): δ 8.35 (1H, d, J=2.8 Hz), 8.17-8.14 (1H, m), 7.44-7.38 (1H, m), 7.25-7.19 (2H, m), 7.10-7.06 (1H, m), 7.03 (1H, d, J=9.2 Hz), 5.26 (2H, s).

Step 2: 3-chloro-4-(3-fluorobenzyloxy)-aniline

The 2-chloro-1-(3-fluorobenzyloxy)-4-nitrobenzene (3.2 g, 11.4 mmol), zinc powder (4.5 g, 68.4 mmol) and ammonium chloride (1.52 g, 28.5 mmol) were added into a mixed solution of ethanol (60 mL) and H₂O (10 mL). The mixture was stirred at 60° C. overnight. Then the reaction mixture was poured into 200 mL of H₂O, extracted with ethyl acetate. The organic phase was separated, washed with saturated brine, and dried. The solvent was removed in vacuo. The compound shown in the title (2.8 g, 98%) was obtained.
¹H NMR (CDCl₃): δ 7.36-7.30 (1H, m), 7.22-7.18 (2H, m), 7.02-6.97 (1H, m), 6.79-6.76 (2H, m), 6.52-6.49 (1H, m), 5.03 (2H, s), 3.49 (2H, br).

Step 3: N-(3-chloro-4-(3-fluorobenzyloxy)phenyl)-7-methoxy-6-nitroquinazoline-4-amine The 3-chloro-4-(3-fluorobenzyloxy)-aniline (2.82 g, 11.1 mmol), 4-chloro-7-methoxy-6-nitroquinazoline (2.68 g, 11.2 mmol) were added into isopropanol (30 mL), stirred at 60° C. for 3 h. Then the solution was filtered, washed with isopropanol and dried, and the compound shown in the title (4.8 g, 95%) was obtained.
¹H NMR (DMSO-d6): δ 10.94 (1H, br), 9.33 (1H, s), 8.79 (1H, s), 7.91 (1H, d, J=2.4 Hz), 7.64-7.61 (1H, m), 7.47-7.40 (2H, m), 7.31-7.27 (3H, m), 7.18-7.13 (1H, m), 5.25 (2H, s), 4.06 (3H, s).

Step 4: N⁴-(3-chloro-4-(3-fluorobenzyloxy)phenyl)-7-methoxy-quinazoline-4,6-diamine A mixture of N-(3-chloro-4-(3-fluorobenzyloxy)phenyl)-7-methoxy-6-nitroquinazoline-4-amine (4.8 g, 10.5 mmol), iron powder (3.54 g, 63 mmol), acetic acid (6 mL) and ethanol (60 mL) was stirred at 85° C. overnight. Then the reaction mixture was poured into 300 mL of H₂O, filtered to obtain the crude product. The crude product was washed with ethyl acetate, filtered and dried, and the compound shown in the title (3.8 g, 85%) was obtained.
¹H NMR (DMSO-d6): δ 10.70 (1H, br), 8.68 (1H, s), 7.84 (1H, d, J=2.4 Hz), 7.59-7.45 (3H, m), 7.32-7.30 (3H, m), 7.19-7.16 (2H, m), 5.93 (2H, br), 5.29 (2H, s), 4.02 (3H, s).

Step 5: tert-butyl 4-(4-(3-chloro-4-(3-fluorobenzyloxy)phenylamino)-7-methoxyquinazoline-6-ylamino)piperidine-1-carboxylate With a method similar with that described in Step 1, Example 2, the compound shown in the title was synthesized from N⁴-(3-chloro-4-(3-fluorobenzyloxy)phenyl)-7-methoxy-quinazoline-4,6-diamine.
¹H NMR (CDCl₃): δ 8.47 (1H, s), 7.78 (1H, d, J=2.4 Hz), 7.58-7.55 (1H, m), 7.40-7.35 (1H, m), 7.26-7.22 (2H, m), 7.17 (1H, s), 7.06-7.01 (1H, m), 6.97 (1H, d, J=8.8 Hz), 6.71 (1H, br), 5.16 (2H, s), 4.68 (1H, d, J=8.0 Hz), 4.10-4.05 (2H, m), 3.96 (3H, s), 3.68 (1H, br), 3.11-3.04 (2H, m), 2.15-2.11 (2H, m), 1.52-1.43 (11H, m).

Step 6: N⁴-(3-chloro-4-(3-fluorobenzyloxy)phenyl)-7-methoxy-N⁶-(piperidin-4-yl)quinazoline-4,6-diamine With a method similar with that described in Step 2, Example 4, the compound shown in the title was synthesized from tert-butyl 4-(4-(3-chloro-4-(3-fluorobenzyloxy)phenylamino)-7-methoxyquinazoline-6-ylamino)piperidine-1-carboxylate.
¹H NMR (DMSO-d6): δ 9.62 (1H, s), 8.29 (1H, s), 8.07 (1H, s), 7.82 (1H, d, J=9.2 Hz), 7.55 (1H, s), 7.49-7.43 (1H, m), 7.33-7.29 (2H, m), 7.23-7.14 (2H, m), 7.05 (1H, s), 5.23 (2H, s), 5.14 (1H, d, J=8.4 Hz), 4.04-4.00 (1H, m), 3.95 (3H, s), 3.12-3.09 (2H, m), 2.92-2.86 (2H, m), 2.05-2.01 (2H, m), 1.53-1.50 (2H, m).

Step 7: 1-(4-(4-(3-chloro-4-(3-fluorobenzyloxy) phenylamino)-7-methoxyquinazoline-6-ylamino) piperidin-1-yl)prop-2-ene-1-one With a method similar with that described in Step 3, Example 2, the compound shown in the title was synthesized from N⁴-(3-chloro-4-(3-fluorobenzyloxy)phenyl)-7-methoxy-N⁶-(piperidin-4-yl)quinazoline-4,6-diamine.
¹H NMR (DMSO-d6): δ 9.14 (1H, s), 8.30 (1H, s), 7.90 (1H, d, J=2.8 Hz), 7.67-7.64 (1H, m), 7.32-7.23 (4H, m), 7.19-7.14 (1H, m), 7.06 (1H, s), 6.87-6.80 (1H, m), 6.12-6.07 (1H, m), 5.68-5.65 (1H, m), 5.27 (1H, d, J=8.4 Hz), 5.24 (1H, s), 4.44-4.38 (1H, m), 4.12-4.07 (1H, m), 3.94 (3H, s), 3.81-3.77 (1H, m), 2.92-2.83 (1H, m), 2.07-2.02 (2H, m), 1.46-1.40 (2H, m).

Example 8 Synthesis of 1-(4-(4-(3-chloro-4-(pyridin-2-ylmethoxy)phenylamino)-7-methoxyquinazoline-6-ylamino)piperidin-1-yl)prop-2-ene-1-one (Compound E8)

Step 1: 2-((2-chloro-4-nitrophenoxy)methyl)pyridine 2-chloro-4-nitrophenol (3.4 g, 20 mmol), 2-(chloromethyl)pyridine hydrochloride (3.4 g, 21 mmol), potassium carbonate (3.3 g, 24 mmol) and sodium iodide (3.0 g, 20 mmol) were refluxed in acetonitrile (30 mL) overnight. The reaction mixture was poured into 100 mL of $H_2O$, extracted with ethyl acetate. The organic phase was washed with saturated brine, dried, evaporated with rotary evaporator, to obtain the crude product. The crude product was washed with petroleum ether, filtered and dried, and the compound shown in the title (3.9 g, 74%) was obtained.

$^1$H NMR (CDCl$_3$): δ 8.63 (1H, d, J=4.8 Hz), 8.34 (1H, d, J=2.8 Hz), 8.16-8.14 (1H, m), 7.79-7.76 (1H, m), 7.62-7.60 (1H, m), 7.31-7.27 (1H, m), 7.11 (1H, d, J=9.2 Hz), 5.49 (2H, s).

Step 2: 3-chloro-4-(pyridin-2-ylmethoxy)aniline

The 2-((2-chloro-4-nitrophenoxy)methyl)pyridine (3.9 g, 15 mmol), zinc powder (5.8 g, 88 mmol) and ammonium chloride (2.4 g, 44 mmol) were added into a mixed solution of ethanol (60 mL) and $H_2O$ (10 mL). The mixture was stirred at 60° C. overnight. Then the reaction mixture was poured into 200 mL of $H_2O$, extracted with ethyl acetate. The organic phase was separated, washed with saturated brine and dried. The solvent was removed in vacuo, and the compound shown in the title (3.4 g, 98%) was obtained.

$^1$H NMR (CDCl$_3$): δ 8.57 (1H, d, J=4.8 Hz), 7.75-7.70 (1H, m), 7.65-7.63 (1H, m), 7.23-7.20 (1H, m), 6.81 (1H, d, J=9.2 Hz), 6.77 (1H, d, J=2.8 Hz), 5.18 (2H, s), 3.48 (2H, br).

Step 3: N-(3-chloro-4-(pyridin-2-ylmethoxy)phenyl)-7-methoxy-6-nitroquinazoline-4-amine The 3-chloro-4-(pyridin-2-ylmethoxy)aniline (3.5 g, 14 mmol), 4-chloro-7-methoxy-6-nitroquinazoline (3.4 g, 14 mmol) were added into isopropanol (40 mL), stirred at 60° C. for 3 h. Then the solution was filtered; the filter cake was washed with isopropanol, dried, and the compound shown in the title (5.6 g, 92%) was obtained.

$^1$H NMR (DMSO-d6): δ 10.91 (1H, br), 9.34 (1H, s), 8.80 (1H, s), 8.63 (1H, d, J=4.4 Hz), 7.97-7.91 (2H, m), 7.68-7.61 (2H, m), 7.50 (1H, s), 7.44-7.40 (1H, m), 7.34 (1H, d, J=9.2 Hz), 5.34 (2H, s), 4.09 (3H, s).

Step 4: N$^4$-(3-chloro-4-(pyridin-2-ylmethoxy)phenyl)-7-methoxyquinazoline-4,6-diamine A mixture of N-(3-chloro-4-(pyridin-2-ylmethoxy)phenyl)-7-methoxy-6-nitroquinazoline-4-amine (5.6 g, 13 mmol), iron powder (4.5 g, 81 mmol), acetic acid (8 mL) and ethanol (60 mL) was stirred at 85° C. overnight. Then the mixture was poured into 300 mL of $H_2O$, filtered to obtain the crude product. The crude product was washed with ethyl acetate, filtered and dried, and the compound shown in the title (4.5 g, 86%) was obtained.

$^1$H NMR (DMSO-d6): δ 10.66 (1H, br), 8.67 (1H, s), 8.59 (1H, d, J=4.4 Hz), 7.90-7.84 (2H, m), 7.58-7.54 (2H, m), 7.51 (1H, s), 7.38-7.35 (1H, m), 7.30 (1H, d, J=9.2 Hz), 7.15 (1H, s), 5.92 (2H, br), 5.31 (2H, s), 4.00 (3H, s).

Step 5: tert-butyl 4-(4-(3-chloro-4-(pyridin-2-ylmethoxy)phenylamino-7-methoxyquinazoline-6-ylamino)piperidine-1-carboxylate With a method similar with that described in Step 1, Example 2, the compound shown in the title was synthesized from N$^4$-(3-chloro-4-(pyridin-2-ylmethoxy)phenyl)-7-methoxyquinazoline-4,6-diamine.

$^1$H NMR (CDCl$_3$): δ 8.60 (1H, d, J=4.8 Hz), 8.50 (1H, s), 7.77-7.73 (2H, m), 7.66 (1H, d, J=7.6 Hz), 7.49-7.46 (1H, m), 7.26-7.23 (1H, m), 7.16 (1H, s), 7.00 (1H, d, J=8.8 Hz), 6.61 (1H, br), 5.28 (2H, s), 4.64 (1H, d, J=8.0 Hz), 4.08-3.98 (5H, m), 3.62-3.59 (1H, m), 3.06-3.00 (2H, m), 2.11-2.07 (2H, m), 1.49-1.46 (11H, m).

Step 6: N$^4$-(3-chloro-4-(pyridin-2-ylmethoxy)phenyl)-7-methoxy-N$^6$-(piperidin-4-yl)quinazoline-4,6-diamine With a method similar with that described in Step 2, Example 4, the compound shown in the title was synthesized from tert-butyl 4-(4-(3-chloro-4-(pyridin-2-ylmethoxy)phenylamino-7-methoxyquinazoline-6-ylamino)piperidine-1-carboxylate.

Step 7: 1-(4-(4-(3-chloro-4-(pyridin-2-ylmethoxy)phenylamino)-7-methoxyquinazoline-6-ylamino)piperidin-1-yl)prop-2-ene-1-one With a method similar with that described in Step 3, Example 2, the compound shown in the title was synthesized from N$^4$-(3-chloro-4-(pyridin-2-ylmethoxy)phenyl)-7-methoxy-N$^6$-(piperidin-4-yl)quinazoline-4,6-diamine.

$^1$H NMR (DMSO-d6): δ 8.60 (1H, d, J=4.8 Hz), 8.47 (1H, s), 7.78-7.74 (2H, m), 7.66-7.64 (1H, m), 7.49-7.47 (1H, m), 7.26-7.24 (1H, m), 7.16 (1H, s), 6.97 (1H, d, J=8.8 Hz), 6.79 (1H, br), 6.63-6.56 (1H, m), 6.32-6.27 (1H, m), 5.72-5.69 (1H, m), 5.26 (2H, s), 4.65 (1H, d, J=8.0 Hz), 4.55-4.50 (1H, m), 4.01-3.95 (4H, m), 3.76-3.74 (1H, m), 3.36-3.29 (1H, s), 3.08-3.00 (1H, m), 2.22-2.14 (2H, m), 1.52-1.46 (2H, m).

Example 9 Synthesis of 1-(3-(4-(3-chloro-4-(pyridin-2-ylmethoxy)phenylamino)-7-methoxyquinazoline-6-ylamino)azetidin-1-yl)prop-2-ene-1-one (Compound E9)

Step 1: benzyl 3-(4-(3-chloro-4-(pyridin-2-ylmethoxy)phenylamino-7-methoxyquinazoline-6-ylamino)azetidine-1-carboxylate With a method similar with that described in Step 6, Example 1, the compound shown in the title was synthesized from N$^4$-(3-chloro-4-(pyridin-2-ylmethoxy)phenyl)-7-methoxyquinazoline-4,6-diamine.

Step 2: N$^4$-(3-chloro-4-(pyridin-2-ylmethoxy)phenyl)-7-methoxy-N$^6$-(azetidin-3-yl)quinazoline-4,6-diamine With a method similar with that described in Step 7, Example 1, the compound shown in the title was synthesized from benzyl 3-(4-(3-chloro-4-(pyridin-2-ylmethoxy)phenylamino-7-methoxyquinazoline-6-ylamino)azetidine-1-carboxylate.

Step 3: 1-(3-(4-(3-chloro-4-(pyridin-2-ylmethoxy) phenylamino)-7-methoxyquinazoline-6-ylamino) azetidin-1-yl)prop-2-ene-1-one With a method similar with that described in Step 3, Example 2, the compound shown in the title was synthesized from N$^4$-(3-chloro-4-(pyridin-2-ylmethoxy)phenyl)-7-methoxy-N$^6$-(azetidin-3-yl)quinazoline-4,6-diamine.

$^1$H NMR (DMSO-d6): δ 8.58 (1H, d, J=4.8 Hz), 8.45 (1H, s), 8.30 (1H, br), 7.77-7.75 (2H, m), 7.64-7.62 (1H, m), 7.51-7.48 (1H, m), 7.26-7.24 (1H, m), 7.18 (1H, s), 6.92 (1H, d, J=9.2 Hz), 6.79 (1H, s), 6.35-6.30 (1H, m), 6.22-6.15 (1H, m), 5.69-5.66 (1H, m), 5.23 (2H, s), 5.05 (1H, d, J=6.8 Hz), 4.69-4.53 (3H, m), 4.08-4.04 (1H, m), 3.99-3.95 (4H, m).

Example 10 Synthesis of N$^6$-(1-acryloylpiperidin-4-yl)-N$^4$-(3-ethynylphenyl)-7-methoxyquinazoline-4,6-diamine (Compound E10)

Step 1: N-(3-ethynylphenyl)-7-methoxy-6-nitroquinazoline-4-amine

The 4-chloro-7-methoxy-6-nitroquinazoline (1.00 g, 4.17 mmol) was added into a solution of 3-ethynylaniline (0.49 g, 4.17 mmol) in isopropanol (15 mL), refluxed with heating for 1 h. Once the reaction was complete, the solution was cooled and filtered, and the compound shown in the title (1.12 g, 84%) was obtained.

$^1$H NMR (DMSO-d6): δ 11.08 (1H, br), 9.47 (1H, s), 8.89 (1H, s), 7.95 (1H, s), 7.79-7.82 (1H, m), 7.56 (1H, s), 7.47-7.52 (1H, m), 7.37-7.40 (1H, m), 4.27 (1H, s), 4.10 (3H, s).

Step 2: N$^4$-(3-ethynylphenyl)-7-methoxyquinazoline-4,6-diamine

At room temperature, a saturated solution of ammonium chloride (10 mL) was slowly added dropwise into a suspension of iron powder (1.00 g, 17.9 mmol) and N-(3-ethynylphenyl)-7-methoxy-6-nitroquinazoline-4-amine (1.12 g, 3.5 mmol) in ethanol (30 mL). When the addition was complete, the temperature was increased slowly, and the mixture was refluxed with heating for 4 h. Once the reaction was complete, the mixture was cooled and concentrated in vacuo. The residue was added into N,N-dimethylformamide (40 mL), then stirred for 30 min, filtered over diatomaceous earth. The filtrate was concentrated under reduced pressure till dried. The residue was made into slurry with H$_2$O, filtered, washed with H$_2$O and dried, then yellow solid (0.78 g, 86%) was obtained.

$^1$H NMR (DMSO-d6): δ 9.77 (1H, br), 8.49 (1H, s), 7.99 (1H, s), 7.81-7.84 (1H, m), 7.46 (1H, s), 7.37-7.41 (1H, m), 7.20-7.23 (1H, m), 7.12 (1H, s), 5.56 (2H, br), 4.19 (1H, s), 3.99 (3H, s).

Step 3: benzyl 4-{[4-(3-ethynylphenylamino)-7-methoxyquinazolin-6-yl]amino}piperidine-1-carboxylate With a method similar with that described in Step 6, Example 1, the compound shown in the title was synthesized from N$^4$-(3-ethynylphenyl)-7-methoxyquinazoline-4,6-diamine and benzyl 4-oxopiperidine-1-carboxylate.

Step 4: N$^4$-(3-ethynylphenyl)-7-methoxy-N$^6$-(piperidin-4-yl)quinazoline-4,6-diamine The 40% aqueous solution of potassium hydroxide (4 mL) was added into a solution of benzyl 4-{[4-(3-ethynylphenylamino)-7-methoxyquinazoline-6-yl]amino}piperidine-1-carboxylate (200 mg, 0.39 mmol) in ethanol (5 mL), heated to 100° C., and stirred for 3 h. Once the reaction was complete, H$_2$O was slowly added, then extracted with ethyl acetate. The resulting organic phase was washed with saturated brine, dried over anhydrous sodium sulfate, and concentrated in vacuo. The residue was made into slurry with ethyl ether, filtered, and the compound shown in the title (116 mg, 79%) was obtained.

$^1$H NMR (DMSO-d6): δ 9.17 (1H, s), 8.36 (1H, s), 7.98 (1H, s), 7.89-7.91 (1H, m), 7.36-7.40 (1H, m), 7.28 (1H, s), 7.16-7.19 (1H, m), 7.09 (1H, s), 5.10 (1H, d, J=8.8 Hz), 4.19 (1H, s), 3.98 (3H, s), 3.62-3.72 (1H, m), 2.97-3.02 (2H, m), 2.64-2.71 (2H, m), 1.96-2.01 (2H, m), 1.30-1.40 (2H, m).

Step 5: N$^6$-(1-acryloylpiperidin-4-yl)-N$^4$-(3-ethynylphenyl)-7-methoxyquinazoline-4,6-diamine With a method similar with that described in Step 3, Example 2, the compound shown in the title was synthesized from N$^4$-(3-ethynylphenyl)-7-methoxy-N$^6$-(piperidin-4-yl)quinazoline-4,6-diamine.

$^1$H NMR (DMSO-d6): δ 9.13 (1H, s), 8.38 (1H, s), 7.97 (1H, s), 7.90-7.93 (1H, m), 7.37-7.41 (1H, m) 7.31 (1H, s), 7.18-7.21 (1H, m), 7.10 (1H, s), 6.81-6.89 (1H, m), 6.09-6.13 (1H, m), 5.66-5.70 (1H, m), 5.34 (1H, d, J=8.8 Hz), 4.40-4.44 (1H, m), 4.19 (1H, s), 4.08-4.13 (1H, m), 3.97 (3H, s), 3.81-3.88 (1H, m), 2.82-2.91 (2H, m), 2.02-2.11 (2H, m), 1.40-1.48 (2H, m).

Example 11 Synthesis of N$^6$-(1-acryloylazetidin-3-yl)-N$^4$-(3-ethynylphenyl)-7-methoxyquinazoline-4,6-diamine (Compound E11)

Step 1: benzyl 3-{[4-(3-ethynylphenylamino)-7-methoxyquinazolin-6-yl]amino}azetidine-1-carboxylate With a method similar with that described in Step 6, Example 1, the compound shown in the title was synthesized from N$^4$-(3-ethynylphenyl)-7-methoxyquinazoline-4,6-diamine.

$^1$H NMR (CDCl$_3$): δ 8.54 (1H, s), 7.81 (1H, s), 7.71-7.73 (1H, m), 7.22-7.38 (8H, m) 7.14 (1H, s), 6.44 (1H, s), 5.10 (2H, s), 5.01-5.04 (1H, m), 4.43-4.49 (2H, m), 4.32-4.40 (1H, m), 3.99 (1H, s), 3.96 (3H, s), 3.89-3.94 (2H, m).

Step 2: N$^6$-(azetidin-3-yl)-N$^4$-(3-ethynylphenyl)-7-methoxyquinazoline-4,6-diamine With a method similar with that described in Step 7, Example 1, the compound shown in the title was synthesized from benzyl 3-{[4-(3-ethynylphenylamino)-7-methoxyquinazoline-6-yl]amino}azetidine-1-carboxylate.

Step 3: N$^6$-(1-acryloylazetidin-3-yl)-N$^4$-(3-ethynylphenyl)-7-methoxyquinazoline-4,6-diamine With a method similar with that described in Step 3, Example 2, the compound shown in the title was synthesized from N$^6$-(azetidin-3-yl)-N$^4$-(3-ethynylphenyl)-7-methoxyquinazoline-4,6-diamine.

¹H NMR (CD₃OD): δ8.40 (1H, s), 7.83 (1H, s), 7.70-7.72 (1H, m), 7.31-7.38 (2H, m), 7.24-7.27 (1H, m), 7.04 (1H, s), 6.34-6.38 (1H, m), 6.22-6.27 (1H, m), 5.72-5.75 (1H, m), 4.80-4.82 (2H, m), 4.54-4.58 (2H, m), 4.20-4.23 (1H, m), 3.98-4.03 (4H, m).

Example 12 Synthesis of N⁴-(3-acetylphenyl)-N⁶-(1-acryloylpiperidin-4-yl)-7-methoxyquinazoline-4,6-diamine (Compound E12)

Step 1: N⁴-(3-acetylphenyl)-7-methoxy-N⁶-(piperidin-4-yl)quinazoline-4,6-diamine With reference to the method in Step 1, Example 10, N-(3-acetylphenyl)-7-methoxy-6-nitroquinazoline-4-amine was prepared from 4-chloro-7-methoxy-6-nitroquinazoline and 3-acetylaniline. Then sequentially with reference to the methods in Step 2-4, Example 10, the compound in the title was prepared.

Step 2: N⁴-(3-acetylphenyl)-N⁶-(1-acryloylpiperidin-4-yl)-7-methoxyquinazoline-4,6-diamine With a method similar with that described in Step 3, Example 2, the compound shown in the title was synthesized from N⁴-(3-acetylphenyl)-7-methoxy-N⁶-(piperidin-4-yl)quinazoline-4,6-diamine.
¹H NMR (CDCl₃): δ 8.58 (1H, s), 8.20-8.22 (1H, m), 8.10 (1H, s), 7.69-7.72 (1H, m), 7.50-7.54 (1H, m), 7.18-7.21 (2H, m), 6.59-6.62 (2H, m), 6.28-6.333 (1H, m), 5.70-5.75 (1H, m), 4.69 (1H, d, J=7.2 Hz), 4.50-4.57 (1H, m), 4.00-4.03 (4H, m), 3.73-3.80 (1H, m), 3.34-3.42 (1H, m), 3.07-3.14 (1H, m), 2.65 (3H, s), 2.17-2.24 (2H, m), 1.40-1.48 (2H, m).

Example 13 Synthesis of N⁴-(3-acetylphenyl)-N⁶-(1-acryloylazetidin-3-yl)-7-methoxyquinazoline-4,6-diamine (Compound E13)

Step 1: N⁴-(3-acetylphenyl)-N⁶-(azetidin-3-yl)-7-methoxyquinazoline-4,6-diamine

With a method similar with that described in Step 2, Example 10, N-(3-acetylphenyl)-7-methoxy-quinazoline-4,6-diamine was prepared from N-(3-acetylphenyl)-7-methoxy-6-nitroquinazoline-4-amine. Then sequentially with a method similar with those in Step 6 and 7, Example 1, the compound shown in the title was synthesized.
¹H NMR (DMSO-d6): δ 10.85 (1H, s), 9.24 (1H, br), 8.98 (1H, br), 8.75 (1H, s), 8.17 (1H, s), 7.96-8.00 (1H, m), 7.90-7.94 (1H, m), 7.33 (1H, s), 7.25 (1H, s), 6.95-6.98 (1H, m), 4.50-4.56 (1H, m), 4.41-4.44 (2H, m), 4.04-4.11 (5H, m).

Step 2: N⁴-(3-acetylphenyl)-N⁶-(1-acryloylazetidin-3-yl)-7-methoxyquinazoline-4,6-diamine With a method similar with that described in Step 3, Example 2, the compound shown in the title was synthesized from N⁴-(3-acetylphenyl)-N⁶-(azetidin-3-yl)-7-methoxyquinazoline-4,6-diamine.
¹H NMR (CDCl₃): δ 8.60 (1H, s), 8.14-8.20 (2H, m), 7.68-7.72 (1H, m), 7.47-7.52 (1H, m), 6.64 (1H, s), 6.31-6.36 (1H, m), 6.17-6.25 (1H, m), 5.66-5.70 (1H, m), 5.13 (1H, d, J=6.8 Hz), 4.50-4.73 (3H, m), 3.90-4.12 (4H, m), 2.62 (3H, s).

Example 14 Synthesis of N⁶-(1-acryloylazetidin-3-yl)-N⁴-(3-bromophenyl)-7-methoxyquinazoline-4,6-diamine (Compound E14)

Step 1: N-(3-bromophenyl)-7-methoxy-6-nitroquinazoline-4-amine

With a method similar with that described in Step 1, Example 3, the compound shown in the title was synthesized from 4-chloro-7-methoxy-6-nitroquinazoline and 3-bromoaniline.
¹H NMR (DMSO-d6): δ 11.10 (1H, br), 9.43 (1H, s), 8.87 (1H, s), 8.04-8.05 (1H, m), 7.74-7.78 (1H, m), 7.52 (1H, s), 7.38-7.44 (2H, m), 4.07 (3H, s).

Step 2: N⁴-(3-bromophenyl)-7-methoxyquinazoline-4,6-diamine

With a method similar with that described in Step 4, Example 7, the compound shown in the title was synthesized from N-(3-bromophenyl)-7-methoxy-6-nitroquinazoline-4-amine.
¹H NMR (DMSO-d6): δ 10.09 (1H, br), 8.57 (1H, s), 8.05 (1H, s), 7.72-7.75 (1H, m), 7.47 (1H, s), 7.30-7.38 (2H, m), 7.13 (1H, s), 5.62 (2H, br), 3.97 (3H, s).

Step 3: benzyl 3-{[4-(3-bromophenylamino)-7-methoxyquinazoline-6-yl]amino}azetidine-1-carboxylate With a method similar with that described in Step 6, Example 1, the compound shown in the title was synthesized from N⁴-(3-bromophenyl)-7-methoxyquinazoline-4,6-diamine.

Step 4: N⁶-(azetidin-3-yl)-N⁴-(3-bromophenyl)-7-methoxyquinazoline-4,6-diamine

With a method similar with that described in Step 7, Example 1, a trifluoroacetate salt of the compound shown in the title was synthesized from benzyl 3-{[4-(3-bromophenylamino)-7-methoxyquinazoline-6-yl]amino}azetidine-1-carboxylate.
¹H NMR (DMSO-d6): δ 10.40 (1H, br), 8.97 (1H, br), 8.72 (1H, br), 8.66 (1H, s), 7.95 (1H, s), 7.68-7.71 (1H, m), 7.38-7.45 (2H, m), 7.16-7.19 (2H, m), 6.80-6.82 (1H, m), 4.44-4.56 (1H, m), 4.38-4.43 (2H, m), 3.99-4.08 (5H, m).

Step 5: N⁶-(1-acryloylazetidin-3-yl)-N⁴-(3-bromophenyl)-7-methoxyquinazoline-4,6-diamine With a method similar with that described in Step 3, Example 2, the compound shown in the title was synthesized from the trifluoroacetate salt of N⁶-(azetidin-3-yl)-N⁴-(3-bromophenyl)-7-methoxyquinazoline-4,6-diamine.
¹H NMR (DMSO-d6): δ 9.23 (1H, s), 8.38 (1H, s), 8.08 (1H, s), 7.82-7.85 (1H, m), 7.29-7.34 (1H, m), 7.22-7.25 (1H, m), 7.10 (1H, s), 7.03 (1H, s), 6.30-6.38 (2H, m), 6.07-6.12 (1H, m), 5.62-5.67 (1H, m), 4.65-4.68 (1H, m), 4.38-4.51 (2H, m), 4.09-4.13 (1H, m), 3.90-3.96 (4H, m).

Example 15 Synthesis of N⁶-(1-acryloylpiperidin-4-yl)-N⁴-(3-bromophenyl)-7-methoxyquinazoline-4,6-diamine (Compound E15)

Step 1: benzyl 4-{[4-(3-bromophenylamino)-7-methoxyquinazoline-6-yl]amino}piperidine-1-carboxylate With a method similar with that described in Step 3, Example 10, the compound shown in the title was synthesized from N⁴-(3-bromophenyl)-7-methoxyquinazoline-4,6-diamine.

1H NMR (DMSO-d6): δ 9.42 (1H, br), 8.44 (1H, s), 8.10 (1H, s), 7.84 (1H, d, J=8.0), 7.29-7.39 (8H, m), 7.11 (1H, s), 5.40-5.42 (1H, m), 5.10 (2H, s), 4.04-4.08 (2H, m), 3.99 (3H, s), 3.75-3.81 (1H, m), 3.00-3.15 (2H, m), 1.98-2.05 (2H, m), 4.42-1.48 (2H, m).

Step 2: $N^4$-(3-bromophenyl)-7-methoxy-$N^6$-(piperidin-4-yl)quinazoline-4,6-diamine With a method similar with that described in Step 7, Example 1, a trifluoroacetate salt of the compound shown in the title was synthesized from benzyl 4-{[4-(3-bromophenylamino)-7-methoxyquinazoline-6-yl]amino}piperidine-1-carboxylate.
$^1$H NMR (DMSO-d6): δ 10.40 (1H, br), 8.70 (1H, s), 8.61 (1H, br), 8.44 (1H, br), 7.97 (1H, s), 7.72-7.74 (1H, m), 7.42-7.498 (2H, m), 7.38 (1H, s), 7.19 (1H, s), 6.02-6.05 (1H, m), 4.04 (3H, s), 3.75-3.80 (1H, m), 3.32-3.38 (2H, m), 2.98-3.04 (2H, m), 2.12-2.18 (2H, m), 1.70-1.81 (2H, m).

Step 3: $N^6$-(1-acryloylpiperidin-4-yl)-$N^4$-(3-bromophenyl)-7-methoxyquinazoline-4,6-diamine With a method similar with that described in Step 3, Example 2, the compound shown in the title was synthesized from the trifluoroacetate salt of $N^4$-(3-bromophenyl)-7-methoxy-$N^6$-(piperidin-4-yl)quinazoline-4,6-diamine.
$^1$H NMR (DMSO-d6): δ 9.26 (1H, s), 8.39 (1H, s), 8.13 (1H, s), 7.86-7.90 (1H, m), 7.25-7.37 (3H, m), 7.10 (1H, s), 6.82-6.89 (1H, m), 6.09-6.14 (1H, m), 5.66-5.70 (1H, m), 5.37 (1H, d, J=8.8 Hz), 4.39-4.45 (1H, m), 4.09-4.13 (1H, m), 3.97 (3H, s), 3.79-3.88 (1H, m), 3.21-3.27 (1H, m), 2.83-2.92 (1H, m), 2.02-2.09 (2H, m), 1.41-1.50 (2H, m).

Example 16 Synthesis of $N^6$-(1-acryloylazetidin-3-yl)-$N^4$-(3-chloro-4-fluorophenyl)-7-(2-methoxyethoxy)quinazoline-4, 6-diamine (Compound E16)

Step 1: N-(3-chloro-4-fluorophenyl)-7-(2-methoxyethoxy)-6-nitroquinazoline-4-amine With a method similar with that described in Step 2, Example 3, the compound shown in the title was synthesized from N-(3-chloro-4-fluorophenyl)-7-fluoro-6-nitroquinazoline-4-amine and 2-methoxyethanol.
$^1$H NMR (DMSO-d6): δ 10.13 (1H, s), 9.18 (1H, s), 8.65 (1H, s), 8.14 (1H, dd, J=6.8 Hz, 2.4 Hz), 7.75-7.79 (1H, m), 7.49 (1H, s), 7.45 (1H, t, J=9.2 Hz), 4.42 (2H, t, J=4.8 Hz), 3.72 (2H, t, J=4.8 Hz), 3.32 (3H, s).

Step 2: $N^4$-(3-chloro-4-fluorophenyl)-7-(2-methoxyethoxy)quinazoline-4,6-diamine With a method similar with that described in Step 5, Example 1, the compound shown in the title was synthesized from N-(3-chloro-4-fluorophenyl)-7-(2-methoxyethoxy)-6-nitroquinazoline-4-amine.
$^1$H NMR (DMSO-d6): δ 9.38 (1H, s), 8.36 (1H, s), 8.17 (1H, dd, J=6.8 Hz, 2.4 Hz), 7.77-7.81 (1H, m), 7.39 (1H, s), 7.37 (1H, t, J=9.2 Hz), 7.10 (1H, s), 5.29 (2H, s), 4.28 (2H, t, J=4.4 Hz), 3.77 (2H, t, J=4.4 Hz), 3.34 (3H, s).

Step 3: benzyl 3-{[4-(3-chloro-4-fluorophenyl)-7-(2-methoxyethoxy)quinazolin-6-yl]amino}azetidine-1-carboxylate With a method similar with that described in Step 6, Example 1, the compound shown in the title was synthesized from $N^4$-(3-chloro-4-fluorophenyl)-7-(2-methoxyethoxy)quinazoline-4,6-diamine.
$^1$H NMR (CDCl$_3$): δ 8.54 (1H, s), 7.84 (1H, dd, J=6.8 Hz, 2.4 Hz), 7.48-7.52 (1H, m), 7.29-7.37 (5H, m), 7.18 (1H, s), 7.15 (1H, t, J=8.8 Hz), 6.37 (1H, s), 5.09-5.13 (3H, m), 4.47 (2H, dd, J=9.2 Hz, 7.2 Hz), 4.25-4.38 (3H, m), 3.96 (2H, dd, J=9.2 Hz, 4.8 Hz), 3.83 (2H, t, J=4.8 Hz), 3.46 (3H, s).

Step 4: $N^6$-(azetidin-3-yl)-$N^4$-(3-chloro-4-fluorophenyl)-7-(2-methoxyethoxy)quinazoline-4,6-diamine With a method similar with that described in Step 7, Example 1, a trifluoroacetate salt of the compound shown in the title was synthesized from benzyl 3-{[4-(3-chloro-4fluorophenyl)-7-(2-methoxyethoxy)quinazolin-6-yl]amino}azetidine-1-carboxylate.

Step 5: $N^6$-(1-acryloylazetidin-3-yl)-$N^4$-(3-chloro-4-fluorophenyl)-7-(2-methoxyethoxy)quinazoline-4,6-diamine With a method similar with that described in Step 8, Example 1, the compound shown in the title was synthesized from $N^6$-(azetidin-3-yl)-$N^4$-(3-chloro-4-fluorophenyl)-7-(2-methoxyethoxy)quinazoline-4,6-diamine.
$^1$H NMR (DMSO): δ 9.27 (1H, s), 8.37 (1H, s), 8.08 (1H, dd, J=6.8 Hz, 2.4 Hz), 7.75-7.79 (1H, m), 7.42 (1H, t, J=9.2 Hz), 7.14 (1H, s), 7.04 (1H, s), 6.36 (1H, dd, J=17.2 Hz, 10.4 Hz), 6.16 (1H, d, J=6.8 Hz), 6.11 (1H, dd, J=16.4 Hz, 2.4 Hz), 5.66 (1H, dd, J=10.4 Hz, 2.4 Hz), 4.71 (1H, t, J=8.0 Hz), 4.41-4.53 (2H, m), 4.31 (2H, t, J=4.8 Hz), 4.13-4.16 (1H, m), 3.93-3.97 (1H, m), 3.79 (2H, t, J=4.8 Hz), 3.34 (3H, s).

Example 17 Synthesis of $N^6$-(1-acryloylpiperidin-4-yl)-$N^4$-(3-chloro-4-fluorophenyl)-7-(2-methoxyethoxy)quinazoline-4,6-diamine (Compound E17)

Step 1: tert-butyl 4-{[4-(3-chloro-4-fluorophenyl)-7-(2-methoxyethoxy)quinazolin-6-yl]amino}piperidine-1-carboxylate A solution of $N^4$-(3-chloro-4-fluorophenyl)-7-(2-methoxyethoxy)quinazoline-4,6-diamine (100 mg, 0.28 mmol) and tert-butyl 4-oxopiperidine-1-carboxylate (167 mg, 0.84 mmol) in acetic acid (4 mL) was stirred at room temperature for 2 h. Then sodium triacetoxyborohydride (178 mg, 0.84 mmol) was added. After 1 h of reaction, H$_2$O was slowly added to quench the reaction, and the reaction mixture was extracted with ethyl acetate. The resulting organic phase was sequentially washed with H$_2$O, 5% NaHCO$_3$ aqueous solution and saturated brine, dried over anhydrous sodium sulfate, and concentrated in vacuo. The residue was separated through silica column chromatography, and the compound shown in the title (85 mg, 56%) was obtained.
$^1$H NMR (CDCl$_3$): δ 8.52 (1H, s), 7.83 (1H, dd, J=6.8 Hz, 2.4 Hz), 7.51-7.55 (1H, m), 7.17 (1H, s), 7.16 (1H, t, J=8.8 Hz), 6.57 (1H, s), 4.72-4.76 (1H, brs), 4.29 (2H, t, J=4.4 Hz), 4.02-4.11 (2H, m), 3.82 (2H, t, J=4.4 Hz), 3.57-3.64 (1H, m), 3.46 (3H, s), 3.01-3.08 (2H, m), 2.08-2.03 (2H, m), 1.45-1.53 (11H, m).

Step 2: $N^6$-(piperidin-4-yl)-$N^4$-(3-chloro-4-fluorophenyl)-7-(2-methoxyethoxy)quinazoline-4,6-diamine With a method similar with that described in Step 2, Example 4, the compound shown in the title was synthesized from tert-butyl 4-{[4-(3-chloro-4-fluorophenyl)-7-(2-methoxyethoxy) quinazolin-6-yl]amino}piperidine-1-carboxylate.

Step 3: $N^6$-(1-acryloylpiperidin-4-yl)-$N^4$-(3-chloro-4-fluorophenyl)-7-(2-methoxyethoxy)quinazoline-4,6-diamine With a method similar with that described in Step 3, Example 2, the compound shown in the title was synthesized from $N^6$-(piperidin-4-yl)-$N^4$-(3-chloro-4-fluorophenyl)-7-(2-methoxyethoxy)quinazoline-4,6-diamine.

$^1$H NMR (DMSO): δ 9.68-9.75 (1H, brs), 8.40 (1H, s), 8.08 (1H, dd, J=6.8 Hz, 2.4 Hz), 7.75-7.79 (1H, m), 7.42 (1H, t, J=8.8 Hz), 7.40 (1H, s), 7.11 (1H, s), 6.82 (1H, dd, J=16.8 Hz, 10.8 Hz), 6.08 (1H, dd, J=16.8 Hz, 2.4 Hz), 5.65 (1H, dd, J=10.8 Hz, 2.4 Hz), 5.21 (1H, d, J=8.8 Hz), 4.37-4.42 (1H, m), 4.28 (2H, t, J=4.4 Hz), 4.05-4.10 (1H, m), 3.82-3.91 (1H, m), 3.76 (2H, t, J=4.4 Hz), 3.31 (3H, s), 3.20-3.26 (1H, m), 2.85-2.92 (1H, m), 2.00-2.06 (2H, m), 1.35-1.46 (2H, m).

Example 18 Synthesis of $N^6$-(1-acryloylazetidin-3-yl)-$N^4$-(3-chloro-4-fluorophenyl)-7-(2-morpholinylethoxy) quinazoline-4,6-diamine (Compound E18)

Step 1: N-(3-chloro-4-fluorophenyl)-7-(2-morpholinylethoxy)-6-nitroquinazoline-4-amine With a method similar with that described in Step 2, Example 3, the compound shown in the title was synthesized from N-(3-chloro-4-fluorophenyl)-7-fluoro-6-nitroquinazoline-4-amine and 2-morpholineethanol.

$^1$H NMR (DMSO): δ 10.17 (1H, s), 9.19 (1H, s), 8.65 (1H, s), 8.14 (1H, dd, J=6.8 Hz, 2.4 Hz), 7.76-7.80 (1H, m), 7.51 (1H, s), 7.45 (1H, t, J=9.2 Hz), 4.41 (2H, t, J=5.6 Hz), 3.54-3.56 (4H, m), 2.76 (2H, t, J=5.6 Hz), 2.49-2.52 (4H, m).

Step 2: $N^4$-(3-chloro-4-fluorophenyl)-7-(2-morpholinylethoxy)quinazoline-4,6-diamine With a method similar with that described in Step 5, Example 1, the compound shown in the title was synthesized from N-(3-chloro-4-fluorophenyl)-7-(2-morpholinylethoxy)-6-nitroquinazoline-4-amine.

$^1$H NMR (DMSO-d6): δ 9.36 (1H, s), 8.34 (1H, s), 8.15 (1H, dd, J=7.2 Hz, 2.8 Hz), 7.75-7.79 (1H, m), 7.37 (1H, s), 7.36 (1H, t, J=9.2 Hz), 7.09 (1H, s), 5.29 (2H, s), 4.25 (2H, t, J=5.6 Hz), 3.55-3.57 (4H, m), 2.79 (2H, t, J=5.6 Hz), 2.48-2.50 (4H, m).

Step 3: benzyl 3-{[4-(3-chloro-4-fluorophenyl)-7-(2-morpholinylethoxy)quinazolin-6-yl]amino}azetidine-1-carboxylate With a method similar with that described in Step 6, Example 1, the compound shown in the title was synthesized from $N^4$-(3-chloro-4-fluorophenyl)-7-(2-morpholinylethoxy) quinazoline-4,6-diamine.

$^1$H NMR (DMSO-d6): δ 9.36-9.39 (1H, brs), 8.38 (1H, s), 8.11-8.13 (1H, m), 7.79-7.84 (1H, m), 7.43 (1H, t, J=9.2 Hz), 7.30-7.39 (5H, m), 7.16 (1H, s), 7.13 (1H, s), 6.06-6.14 (1H, brs), 5.07 (2H, s), 4.41-4.48 (3H, m), 4.31 (2H, t, J=5.6 Hz), 3.90-4.01 (2H, m), 3.56-3.64 (4H, m), 2.86 (2H, t, J=5.6 Hz), 2.50-2.54 (4H, m).

Step 4: $N^6$-(azetidin-3-yl)-$N^4$-(3-chloro-4-fluorophenyl)-7-(2-morpholinylethoxy)quinazoline-4,6-diamine With a method similar with that described in Step 7, Example 1, a trifluoroacetate salt of the compound shown in the title was synthesized from benzyl 3-{[4-(3-chloro-4-fluorophenyl)-7-(2-morpholinylethoxy)quinazolin-6-yl]amino}azetidine-1-carboxylate.

$^1$H NMR (DMSO-d6): δ 10.32-10.47 (1H, brs), 9.14-9.24 (1H, brs), 9.03-9.12 (1H, brs), 8.63 (1H, s), 7.97 (1H, dd, J=6.8 Hz, 2.4 Hz), 7.65-7.70 (1H, m), 7.49 (1H, t, J=9.2 Hz), 7.31 (1H, s), 7.17 (1H, s), 6.91-6.95 (1H, brs), 4.51-4.64 (3H, m), 4.39-4.48 (2H, m), 4.08-4.16 (2H, m), 3.40-3.97 (10H, m).

Step 5: $N^6$-(1-acryloylazetidin-3-yl)-$N^4$-(3-chloro-4-fluorophenyl)-7-(2-morpholinylethoxy)quinazoline-4,6-diamine With a method similar with that described in Step 3, Example 2, the compound shown in the title was synthesized from the trifluoroacetate salt of $N^6$-(azetidin-3-yl)-$N^4$-(3-chloro-4-fluorophenyl)-7-(2-morpholinylethoxy)quinazoline-4,6-diamine.

$^1$H NMR (DMSO-d6): δ 9.47 (1H, s), 8.37 (1H, s), 8.14 (1H, dd, J=6.8 Hz, 2.4 Hz), 7.82-7.86 (1H, m), 7.41 (1H, t, J=9.2 Hz), 7.18 (1H, S), 7.14 (1H, s), 6.35 (1H, dd, J=13.2 Hz, 9.2 Hz), 6.11 (1H, dd, J=13.2 Hz, 2.4 Hz), 5.66 (1H, dd, J=10.0 Hz, 2.4 Hz), 4.72 (1H, t, J=7.6 Hz), 4.52-4.59 (1H, m), 4.43 (1H, t, J=7.6 Hz), 4.27-4.36 (2H, m), 4.09-4.17 (1H, m), 3.92-3.99 (1H, m), 3.53-3.68 (4H, m), 2.77-2.90 (2H, m), 2.50-2.58 (4H, m).

Example 19 Synthesis of 6-(1-acryloylazetidin-3-yl)-thio-N-(3-chloro-4-fluorophenyl)-7-methoxyquinazoline-4-amine (Compound E19)

Step 1: N-(3-chloro-4-fluorophenyl)-N-(3,4-dimethoxybenzyl)-7-methoxy-6-thiocyanatoquinazoline-4-amine At 0° C., $N^4$-(3-chloro-4-fluorophenyl)-$N^4$-(3,4-dimethoxybenzyl)-7-methoxyquinazoline-4,6-diamine (0.25 g, 0.5 mmol) was slowly added into 30% sulfuric acid (3 g), stirred for 30 min to make it completely dissolved. Sodium nitrite (0.072 g, 1 mmol) was slowly added. The system was stirred at 0° C. for another 30 min, then warmed to room temperature and stirred for 30 min. At room temperature, the solution indicated above was slowly added dropwise into 30 mL aqueous solution of potassium thiocyanate (0.5 g, 5 mmol) and ferric chloride (0.25 g, 1.5 mmol) with vigorous stirring. After the addition, the solution was further stirred overnight, filtered with suction, washed with $H_2O$ and dried. A yellow compound as shown in the title (0.25 g, 92%) was obtained.

$^1$H NMR (DMSO-d6): δ9.03 (1H, s), 7.83 (1H, s), 7.44 (1H, t, J=8.0 Hz), 7.29-7.38 (2H, m), 7.24 (1H, s), 6.92 (1H, s), 6.81 (1H, s), 5.48 (3H, s), 4.05 (3H, s), 3.69 (3H, s), 3.66 (3H, s).

Step 2: tert-butyl 3-{{4-[(3-chloro-4-fluorophenyl)(3,4-dimethoxybenzyl)amino]-7-methoxyquinazoline-6-yl}thio}azetidine-1-carboxylate Sodium borohydride (16 mg, 0.43 mmol) was added into a solution of N-(3-chloro-4-fluorophenyl)-N-(3,4-dimethoxybenzyl)-7-methoxy-6-thiocyanatoquinazoline-4-amine (44 mg, 0.086 mmol) in ethanol (2 mL), stirred at room temperature for 1 h, then additional sodium borohydride (5 mg) was added, and the solution was further stirred for 30 min. When the raw material disappear, as confirmed with TLC, anhydrous potassium carbonate (120 mg) and tert-butyl 3-iodoazetidine-1-carboxylate (30 mg, 0.106 mmol) were sequentially added. Then the mixture was heated to 50° C., and the reaction was allowed to proceed for 5 h. Once the reaction was complete, the solution was cooled, and $H_2O$ was slowly added to quench the reaction, then the solution was extracted with ethyl acetate. The resulting organic phase was sequentially washed with $H_2O$ and saturated brine, dried over anhydrous sodium sulfate, and concentrated in vacuo. The residue was purified with preparative thin layer chromatography (dichloromethane:ethyl acetate (v/v)=1:2), and the compound shown in the title (15 mg, 27%) was obtained.

$^1$H NMR (CDCl$_3$): δ 8.82 (1H, s), 7.38 (1H, br), 7.10-7.20 (2H, m), 6.80-6.93 (2H, m), 6.72-6.77 (3H, m), 5.33 (2H, s), 4.10-4.15 (2H, m), 3.98 (3H, s), 3.84 (3H, s), 3.79 (3H, s), 3.60-6.68 (2H, m), 3.30-3.35 (1H, m), 1.45 (9H, s).

Step 3: 6-(azetidin-3-yl)thio-N-(3-chloro-4-fluorophenyl)-7-methoxyquinazoline-4-amine With a method similar with that described in Step 7, Example 1, a trifluoroacetate salt of the compound shown in the title was synthesized from tert-butyl 3-{{4-[(3-chloro-4-fluorophenyl)(3,4-dimethoxybenzyl)amino]-7-methoxyquinazoline-6-yl}thio}azetidine-1-carboxylate.

$^1$H NMR (DMSO-d6): δ 10.30 (1H, s), 8.97-9.03 (2H, m), 8.64 (1H, s), 8.16 (1H, s), 8.02-8.04 (1H, m), 7.70-7.72 (1H, m), 7.46-7.49 (1H, m), 7.27 (1H, s), 4.42-4.47 (3H, m), 3.99 (3H, s), 3.82-3.88 (3H, m).

Step 4: 6-(1-acryloylazetidin-3-yl)thio-N-(3-chloro-4-fluorophenyl)-7-methoxyquinazoline-4-amine With a method similar with that described in Step 3, Example 2, the compound shown in the title was synthesized from the trifluoroacetate salt of 6-(azetidin-3-yl)thio-N-(3-chloro-4-fluorophenyl)-7-methoxyquinazoline-4-amine.

$^1$H NMR (CD$_3$OD): δ 8.39 (1H, s), 8.03 (1H, s), 7.88-7.90 (1H, m), 7.54-7.56 (1H, m), 7.16-7.20 (1H, m), 7.11 (1H, s), 6.17-6.24 (2H, m), 5.64-5.67 (1H, m), 4.71-4.73 (1H, m), 4.45-4.48 (1H, m), 4.26-4.29 (1H, m), 4.11-4.13 (1H, m), 3.95 (3H, s), 3.86-3.89 (1H, m).

Example 20 Synthesis of 6-(1-acryloylpyrrolidin-3-yl)thio-N-(3-chloro-4-fluorophenyl)-7-methoxyquinazoline-4-amine (Compound E20)

Step 1: tert-butyl 3-{{4-[(3-chloro-4-fluorophenyl)(3,4-dimethoxybenzyl)amino]-7-methoxyquinazoline-6-yl}thio}pyrrolidine-1-carboxylate With a method similar with that described in Step 2, Example 19, the compound shown in the title was synthesized from N-(3-chloro-4-fluorophenyl)-N-(3,4-dimethoxybenzyl)-7-methoxy-6-thiocyanatoquinazoline-4-amine and tert-butyl 3-iodopyrrolidine-1-carboxylate.

$^1$H NMR (CDCl$_3$): δ 8.81 (1H, s), 7.15-7.26 (2H, m), 7.05-7.12 (1H, m), 7.04 (1H, s), 6.95 (1H, s), 6.90-6.94 (1H, m), 6.78-6.82 (1H, m), 6.74-6.77 (1H, m), 5.30-5.35 (2H, m), 3.98 (3H, s), 3.84 (3H, s), 3.79 (3H, s), 3.35-3.60 (3H, m), 3.12-3.21 (2H, m), 1.92-2.05 (1H, m), 1.60-1.70 (1H, m), 1.45 (9H, s).

Step 2: N-(3-chloro-4-fluorophenyl)-7-methoxy-6-(pyrrolidin-1-ylthio)quinazoline-4-amine With a method similar with that described in Step 7, Example 1, a trifluoroacetate salt of the compound shown in the title was synthesized from tert-butyl 3-{{4-[(3-chloro-4-fluorophenyl)(3,4-dimethoxybenzyl)amino]-7-methoxyquinazoline-6-yl}thio}pyrrolidine-1-carboxylate.

$^1$H NMR (DMSO-d6): δ 10.50 (1H, br), 9.03-9.09 (2H, br), 8.73 (1H, s), 8.40 (1H, s), 8.02-8.04 (1H, m), 7.70-7.75 (1H, m), 7.49-7.55 (1H, m), 7.32 (1H, s), 4.22-4.28 (1H, m), 4.04 (3H, s), 3.52-3.80 (3H, m), 3.12-3.20 (1H, m), 2.42-2.50 (1H, m), 1.92-2.01 (1H, m).

Step 3: 6-(1-acryloylpyrrolidin-3-yl)thio-N-(3-chloro-4-fluorophenyl)-7-methoxyquinazoline-4-amine With a method similar with that described in Step 3, Example 2, the compound shown in the title was synthesized from the trifluoroacetate salt of N-(3-chloro-4-fluorophenyl)-7-methoxy-6-(pyrrolidin-1-ylthio)quinazoline-4-amine.

$^1$H NMR (CD$_3$OD): δ 8.46 (1H, s), 8.31-8.34 (1H, m), 7.94-7.98 (1H, m), 7.61-7.65 (1H, m), 7.21-7.26 (1H, m), 7.15 (1H, s), 6.45-6.61 (1H, m), 6.20-6.28 (1H, m), 5.65-5.75 (1H, m), 4.17-4.25 (1H, m), 3.99 (3H, s), 3.79-3.88 (1H, m), 3.65-3.78 (1H, m), 3.35-3.42 (2H, m), 2.30-2.48 (1H, m), 1.90-2.08 (1H, m).

Example 21 Synthesis of 6-(1-acryloylpiperidin-4-yl)thio-N-(3-chloro-4-fluorophenyl)-7-methoxyquinazoline-4-amine (Compound E21)

Step 1: tert-butyl 4-{{4-[(3-chloro-4-fluorophenyl)(3,4-dimethoxybenzyl)amino]-7-methoxyquinazoline-6-yl}thio}piperidine-1-carboxylate With a method similar with that described in Step 2, Example 19, the compound shown in the title was synthesized from N-(3-chloro-4-fluorophenyl)-N-(3,4-dimethoxybenzyl)-7-methoxy-6-thiocyanatoquinazoline-4-amine and tert-butyl 4-iodopiperidine-1-carboxylate.

$^1$H NMR (CDCl$_3$): δ 8.82 (1H, s), 7.10-7.18 (4H, m), 6.88-6.93 (2H, m), 6.78-6.82 (1H, m), 6.74-6.77 (1H, m), 5.33 (2H, s), 3.98 (3H, s), 3.84 (3H, s), 3.79 (3H, s), 2.86-2.96 (3H, m), 1.50-1.70 (4H, m), 1.45 (9H, s), 1.30-1.40 (2H, m).

Step 2: N-(3-chloro-4-fluorophenyl)-6-(piperidin-4-ylthio)-7-methoxyquinazoline-4-amine With a method similar with that described in Step 7, Example 1, a trifluoroacetate salt of the compound shown in the title was synthesized from tert-butyl 4-{{4-[(3-chloro-4-fluorophenyl)(3,4-dimethoxybenzyl)amino]-methoxyquinazoline-6-yl}thio}piperidine-1-carboxylate.

$^1$H NMR (DMSO-d6): δ 10.54 (1H, br), 8.74 (1H, s), 8.63 (1H, br), 8.56 (1H, s), 8.48 (1H, br), 8.05-8.09 (1H, m), 7.72-7.78 (1H, m), 7.48-7.55 (1H, m), 7.30 (1H, s), 4.03 (3H, s), 3.72-3.80 (1H, m), 3.26-3.35 (2H, m), 2.98-3.05 (2H, m), 2.06-2.15 (2H, m), 1.65-1.78 (2H, m).

Step 3: 6-(1-acryloylpiperidin-4-yl)thio-N-(3-chloro-4-fluorophenyl)-7-methoxyquinazoline-4-amine With a method similar with that described in Step 3, Example 2, the compound shown in the title was synthesized from the trifluoroacetate salt of N-(3-chloro-4-fluorophenyl)-6-(piperidin-4-ylthio)-7-methoxyquinazoline-4-amine.

$^1$H NMR (CD$_3$OD): δ 8.46 (1H, s), 8.38 (1H, s), 7.94-7.98 (1H, m), 7.61-7.65 (1H, m), 7.21-7.26 (1H, m), 7.15 (1H, s), 6.69-6.74 (1H, m), 6.14-6.19 (1H, m), 5.68-5.72 (1H, m), 4.24-4.29 (1H, m), 3.98-4.06 (4H, m), 3.68-3.75 (1H, m), 3.30-3.40 (1H, m), 3.12-3.20 (1H, m), 1.97-2.03 (2H, m), 1.50-1.60 (2H, m).

Example 22 Synthesis of (R)-6-(1-acryloylpiperidin-3-yl)thio-N-(3-chloro-4-fluorophenyl)-7-methoxyquinazoline-4-amine (Compound E22)

Step 1: tert-butyl (R)-3-{{4-[(3-chloro-4-fluorophenyl)(3,4-dimethoxybenzyl)amino]-methoxyquinazoline-6-yl}thio}piperidine-1-carboxylate With a method similar with that described in Step 2, Example 19, the compound shown in the title was synthesized from N-(3-chloro-4-fluorophenyl)-N-(3,4-dimethoxybenzyl)-7-methoxy-6-thiocyanatoquinazoline-4-amine and tert-butyl (S)-3-iodopiperidine-1-carboxylate.

$^1$H NMR (CDCl$_3$): δ 8.83 (1H, s), 7.08-7.18 (1H, m), 7.07 (1H, s), 6.85-95 (3H, m), 6.78-6.85 (1H, m), 6.74-6.78 (2H, m), 5.33 (2H, s), 3.97 (3H, s), 3.84 (3H, s), 3.75-3.80 (4H, m), 2.45-3.00 (2H, m), 1.65-1.92 (4H, m), 1.30-1.50 (11H, m).

Step 2: (R)—N-(3-chloro-4-fluorophenyl)-7-methoxy-6-(piperidin-3-ylthio)quinazoline-4-amine With a method similar with that described in Step 7, Example 1, a trifluoroacetate salt of the compound shown in the title was synthesized from tert-butyl (R)-3-{{4-[(3-chloro-4-fluorophenyl)(3,4-dimethoxybenzyl)amino]-7-methoxyquinazoline-6-yl}thio}piperidine-1-carboxylate.

$^1$H NMR (CD$_3$OD): δ 8.65 (1H, s), 8.61 (1H, s), 7.92-7.95 (1H, m), 7.61-7.65 (1H, m), 7.27-7.33 (1H, m), 7.25 (1H, s), 4.09 (3H, s), 3.74-3.80 (1H, m), 3.51-3.58 (2H, m), 2.99-3.06 (2H, m), 2.16-2.22 (1H, m), 2.00-2.06 (1H, m), 1.80-1.92 (2H, m), 1.62-1.73 (1H, m).

Step 3: (R)-6-(1-acryloylpiperidin-3-yl)thio-N-(3-chloro-4-fluorophenyl)-7-methoxyquinazoline-4-amine With a method similar with that described in Step 3, Example 2, the compound shown in the title was synthesized from the trifluoroacetate salt of (R)—N-(3-chloro-4-fluorophenyl)-7-methoxy-6-(piperidin-3-ylthio)quinazoline-4-amine.

$^1$H NMR (CD$_3$OD): δ8.44 (1H, s), 8.22 (1H, s), 8.14-8.17 (1H, m), 7.95-8.00 (1H, m), 7.16-7.20 (1H, m), 7.06 (1H, s), 6.77-6.85 (1H, m), 6.26-6.31 (1H, m), 5.78-5.81 (1H, m), 4.78-4.82 (1H, m), 4.04-4.12 (1H, m), 3.98 (3H, s), 3.38-3.45 (2H, m), 2.73-2.79 (1H, m), 2.12-2.18 (1H, m), 1.93-1.97 (1H, m), 1.62-1.80 (2H, m).

Example 23 Synthesis of N$^6$-(1-acryloylpiperidin-4-yl)-N$^4$-(3-chloro-4-fluorophenyl)-quinazoline-4,6-diamine (Compound E23)

Step 1: 6-nitroquinazoline-4(3H)-one

In ice-water bath, quinazoline-4(3H)-one (1.46 g, 10 mmol) was slowly added in batches into an acid mixture (concentrated sulfuric acid:concentrated nitric acid=4:1) (8 mL). When the addition was complete, the temperature of the system was slowly raised up to 95° C. After 1 h of reaction, the reaction mixture was poured into iced water (100 mL), stirred till solid was precipitated. The mixture was filtered, and the resulting solid was separated through silica column chromatography, then the compound shown in the title (1.45 g, 76%) was obtained.

$^1$H NMR (DMSO-d6): δ 12.90 (1H, br), 8.78 (1H, d, J=2.4 Hz), 8.52 (1H, dd, J=2.4 Hz, 8.8 Hz), 8.28 (1H, s), 7.83 (1H, d, J=8.8 Hz).

Step 2: N$^4$-(3-chloro-4-fluorophenyl)-quinazoline-4,6-diamine

A solution of 6-nitroquinazoline-4(3H)-one (1.34 g, 7.0 mmol) and phosphorus pentachloride (1.46 g, 7.0 mmol) in phosphorus trichloride (5 mL) was stirred for 6 h at 160° C., then cooled to room temperature. The reaction mixture was poured into chilled n-hexane, stirred till solid was precipitated. The mixture was filtered, and the filter cake was washed with ethyl ether, dried in vacuo to obtain white solid. Acetonitrile (20 mL) was added into the mixture of the resulting white solid and 3-chloro-4-fluoro-aniline (1.02 g, 7.0 mmol), then the temperature of the system was slowly raised up to 80° C. After 2 h of reaction, the mixture was cooled to room temperature, while the solvent was evaporated under reduced pressure. After adding saturated NaHCO$_3$ solution (50 mL), the mixture was extracted with ethyl acetate. The resulting organic phase was washed with saturated brine, dried over anhydrous sodium sulfate, and concentrated in vacuo till completely dried. The residue was dissolved in a mixture of DMF:methanol=1:1 (20 mL), then Raney nickel (70 mg) was added into the resulting mixture. The system was replaced with hydrogen gas, and stirred in hydrogen gas atmosphere (1 atm) at 40° C. for 4 h. The mixture was filtered, and the filtrate was concentrated under reduced pressure. The resulting oily product was separated through silica column chromatography, and the target product (303 mg, 15%) was obtained.

$^1$H NMR (DMSO-d6): δ 9.90 (1H, br), 8.45 (1H, s), 8.11-8.09 (1H, m), 7.75-7.73 (1H, m), 7.55-7.53 (1H, m), 7.42-7.39 (1H, m), 7.28-7.27 (1H, m), 5.17 (2H, br).

Step 3: benzyl 4-{{4-[(3-chloro-4-fluorophenyl)amino]-quinazolin-6-yl}amino}piperidine-1-carboxylate With a method similar with that described in Step 6, Example 1, the compound shown in the title was synthesized from N$^4$-(3-chloro-4-fluorophenyl)-quinazoline-4,6-diamine and benzyl 4-oxopiperidine-1-carboxylate.

$^1$H NMR (d6-DMSO): δ 10.63 (1H, br), 8.63 (1H, s), 7.96-7.94 (1H, m), 7.65-7.61 (2H, m), 7.56-7.52 (1H, m), 7.24-7.21 (1H, m), 7.38-7.34 (5H, m), 6.64 (1H, s), 5.07 (2H, s), 3.98-3.95 (2H, m), 3.65-3.62 (1H, m), 3.18-3.14 (2H, m), 1.99-1.95 (2H, m), 1.36-1.34 (2H, m).

Step 4: N⁶-(piperidin-4-yl)-N⁴-(3-chloro-4-fluoro-phenyl)-quinazoline-4,6-diamine With a method similar with that described in Step 7, Example 1, a trifluoroacetate salt of the compound shown in the title was synthesized from benzyl 4-{{4-[(3-chloro-4-fluorophenyl) amino]-quinazolin-6-yl}amino}piperidine-1-carboxylate.

$^1$H NMR (DMSO-d6): δ 10.79 (1H, s), 8.67-8.52 (3H, m), 7.96-7.93 (1H, m), 7.64-7.61 (2H, m), 7.54-7.51 (1H, m), 7.48-7.45 (1H, m), 7.34-7.31 (1H, m), 6.84 (1H, s), 3.70-3.68 (2H, m), 3.04-2.98 (3H, m), 2.14-2.11 (2H, m), 1.66-1.64 (2H, m).

Step 5: N⁶-(1-acryloylpiperidin-4-yl)-N⁴-(3-chloro-4-fluorophenyl)-quinazoline-4,6-diamine With a method similar with that described in Step 3, Example 2, the compound shown in the title was synthesized from the trifluoroacetate salt of N⁶-(piperidin-4-yl)-N⁴-(3-chloro-4-fluorophenyl)-quinazoline-4,6-diamine.

$^1$H NMR (DMSO-d6): δ 9.55 (1H, s), 8.30 (1H, s), 8.16-8.14 (1H, m), 7.84-7.83 (1H, m), 7.46-7.43 (1H, m), 7.42-7.39 (1H, m), 7.31-7.29 (1H, m), 7.24-7.22 (1H, m), 6.85-6.81 (1H, m), 6.15-6.05 (2H, m), 5.66-5.63 (1H, m), 4.29-4.26 (1H, m), 4.02-3.98 (1H, m), 3.84-3.79 (2H, m), 3.01-2.97 (1H, m), 2.02-1.98 (2H, m), 1.20-1.18 (2H, m).

In Vitro Activity Test

1. The Method for In Vitro Enzymology Test

EGFR, EGFR (T790M, L858R), HER2 kinase were expressed and purified through an insect cell expression system by the Department of Biology, Centaurus Biopharma, Beijing, or purchased from commercially available products.

The platform for testing the kinase activity of EGFR, EGFR (T790M, L858R) and HER2 was established based on the homogeneous time-resolved fluorescence (HTRF) method provided by Cisbio Bioassays, and the activity of the compounds was determined with the platform. Starting from 100 nM (for EGFR and HER2) or 1 μM (for EGFR-T790M/L858R), the compounds were diluted in gradient of 3 times with 100% DMSO. For each concentration, 4 μL of solution was taken and added into 96 μL of reaction buffer (50 mM 4-hydroxyethylpiperazineethanesulfonic acid (HEPES)(pH 7.0), 0.02% NaN₃, 0.01% bovine serum albumin (BSA), 0.1 mM Sodium Orthovanadate, 5 mM MgCl₂, 50 nM SEB (Cisbio, Cat No. 61SEBALB), 1 mM DTT). And 2.5 μL of the mixture was taken, added into 384-well plates (Opti-Plate-384, PerkinElmer), then 2.5 μL of kinase was added, mixed thoroughly by centrifuge. Then 5 μL of ATP and TK Substrate-biotin were added to initiate the reaction. The 384-well plates were incubated at 23° C. in an incubator for a certain period of time, then 5 μL of Eu³⁺-Cryptate labeled TK-Antibody and 5 μL of streptavidin-XL665 were added to stop the reaction. After 1 h incubation in an incubator, the fluorescence value was read on Envision (PerkinElmer). The $IC_{50}$ value of the compound was calculated with the software GraphPad Prism 5.0.

2. Proliferation Test of Anchorage-Independent Cells

NCI-H1975, a human non-small cell lung cancer cell, and BT474, a human breast cancer cell line, were incubated with RPIM-1640 or DMEM medium supplemented with 10% fetal bovine serum (FBS) in a cell incubator (37° C., 5% CO₂). In the test of the compounds, the coated substrate with a concentration of 0.6% was used. The cells were screened with 0.3% low melting point agarose, then plated into 96-well plates with a density of 10,000 cells per well (100 μL). Starting from 10 mM, the compounds were diluted in a gradient of 3 times. For each concentration, 2 μL of the solution was taken and added into 98 μL of medium, then 5.3 μL of the mixture was added into the cell culture medium (where the final concentration of DMSO was 0.1%, v/v). After one week (7 days) of treatment, 20 μL of CellTiter-Blue®reagent (Promega) was added, incubated at 37° C. for 4 h. The fluorescent signal was read on Envison (Perkin Elmer). The $IC_{50}$ value, which showed the inhibitory effect of the compounds on cell proliferation, was calculated with GraphPad Prism 5.0.

TABLE

| | Biological activity | | | | |
|---|---|---|---|---|---|
| | Enzyme activity ($IC_{50}$ nM) | | | Cell activity ($IC_{50}$ nM) | |
| Compound | EGFR | EGFR-L858R/T790M | HER2 | H1975 | BT474 |
| Example 1 | 0.3 | 0.8 | 0.5 | 21.8 | 4.2 |
| Example 2 | 0.2 | 2.0 | 0.2 | 14.0 | 2.1 |
| Example 3 | 0.2 | 0.6 | 0.3 | 31.4 | 5.1 |
| Example 4 | 0.4 | 2.1 | 0.4 | 25.6 | 1.6 |
| Example 6 | NT | 52.1 | NT | NT | NT |
| Example 7 | NT | 36.7 | NT | NT | NT |
| Example 8 | 0.6 | 3.7 | 1.2 | 244.2 | 62.1 |
| Example 10 | NT | 8.6 | NT | NT | NT |
| Example 11 | NT | 1.1 | NT | NT | NT |
| Example 12 | NT | 21.2 | NT | NT | NT |
| Example 13 | 0.1 | 5.3 | 0.5 | NT | NT |
| Example 14 | NT | 2.2 | 0.2 | 59.3 | 4.6 |
| Example 15 | 0.3 | 2.9 | 0.2 | 56.0 | 4.2 |
| Example 16 | NT | 1.2 | 0.3 | 32.4 | 8.7 |
| Example 17 | 0.2 | 1.2 | 0.4 | 71.5 | 4.7 |
| Example 18 | NT | 11.1 | NT | NT | NT |
| Example 19 | 0.4 | 11.7 | NT | 274.2 | 97.1 |
| Example 20 | NT | 251.2 | NT | NT | NT |
| Example 21 | NT | 134.4 | NT | NT | NT |
| Example 23 | NT | 19.5 | NT | NT | NT |

Remark:
NT indicates "not determined".

Pharmacokinetics Test on Rats

In this study, 6 healthy adult male rats (from Beijing Vital River Laboratory Animal Technology Co., Ltd.) were used. The animals were fast overnight before the experiment. The fasting period was from 12 h prior to the administration, till 4 h after the administration. Drug administration was performed through gavage at a single dose of 5 mg/kg. The compounds to be tested were dissolved in 20% aqueous solution of sulfobutyl-β-cyclodextrin (SBE). Blood samples were collected 0.25, 0.5, 1, 2, 4, 6, 8 and 24 hours after drug administration. During blood sampling, the animals were lightly anesthetized with isoflurane, and approximately 0.5 mL whole blood was collected from retro-orbital venous sinus, placed into tubes that contain heparin as anticoagulant. The samples were centrifuged at 4° C., 4000 rpm for 5 min. The plasma was transferred into centrifuge tubes, and stored at −80° C. till being analyzed. The drug concentration in the plasma was quantitatively analyzed with liquid chromatography-tandem mass spectrometry (LC-MS/MS). From the analysis result of the samples, the pharmacokinetic parameter of the compounds was calculated with WinNonlin (WinNonlin Professional, version 0.6.3).

| Compound | $T_{1/2}$ (hr) | $T_{max}$ (hr) | $C_{max}$ (ng/mL) | $AUC_{0-\infty}$ (hr * ng/mL) |
|---|---|---|---|---|
| Example 1 | 1.30 | 0.50 | 588 | 1346 |
| Example 2 | 2.39 | 1.00 | 1972 | 11040 |

The invention claimed is:

1. A compound represented by formula (I) or a pharmaceutically acceptable salt thereof,

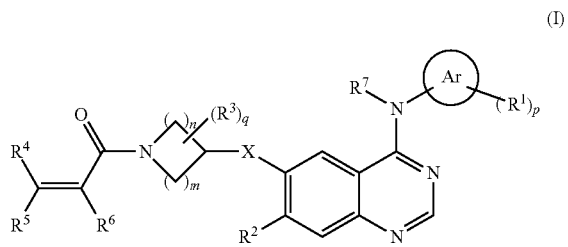

(I)

wherein:
ring Ar is an aryl group or a heteroaryl group;
X is selected from the group consisting of —$NR^8$—, —S—, —S(=O)—, or —S(=O)$_2$—;
n and m are each an integer of 0 to 6, and are not simultaneously 0;
p is an integer of 0 to 5;
q is an integer of 0 to 8;
$R^1$ is independently selected from the group consisting of a $C_{1-6}$ alkyl group, a $C_{3-8}$ cycloalkyl group, a $C_{2-6}$ alkenyl group, a $C_{2-6}$ alkynyl group, a heterocycloalkyl group, a halogen atom, an amino group, a mono($C_{1-6}$ alkyl) amino group, a di($C_{1-6}$ alkyl) amino group, a hydroxy group, a $C_{1-6}$ alkoxy group, a mercapto group, a $C_{1-6}$ alkylthio group, a $C_{1-6}$ alkylcarbonyl group, an aryl group, a heteroaryl group, a cyano group, and a nitro group, wherein the $C_{1-6}$ alkyl group, $C_{1-6}$ alkoxy group, $C_{2-6}$ alkenyl group, and $C_{2-6}$ alkynyl group are optionally substituted by a halogen atom, a cyano group, a nitro group, a $C_{1-6}$ alkoxy group, an aryl group, a heteroaryl group, or a heterocycloalkyl group; and the aryl group, heteroaryl group and heterocycloalkyl group are optionally further substituted by a halogen atom, a cyano group, a nitro group, a $C_{1-6}$ alkyl group, a $C_{1-6}$ alkoxy group, or a $C_{1-6}$ alkylcarbonyl group;
$R^2$ is selected from the group consisting of hydrogen, a hydroxy group, a $C_{1-6}$ alkoxy group, a heterocycloalkyloxy group, and a $C_{1-6}$ alkoxy group substituted by $C_{1-6}$ alkoxy or heterocycloalkyl group;
$R^3$ is independently selected from the group consisting of a halogen atom, a cyano group, a mercapto group, a $C_{1-6}$ alkylthio group, a $C_{1-6}$ alkyl group, a $C_{3-8}$ cycloalkyl group, a heterocycloalkyl group, an amino group, a mono($C_{1-6}$ alkyl)amino group, a di($C_{1-6}$ alkyl) amino group, a hydroxy group, a $C_{1-6}$ alkoxy group, a $C_{1-6}$ alkoxycarbonyl group, a $C_{1-6}$ alkylamido group, a mono($C_{1-6}$ alkyl)aminoacyl group, and a di($C_{1-6}$ alkyl) aminoacyl group;
$R^4$, $R^5$, and $R^6$ are each independently selected from the group consisting of hydrogen, a halogen atom, a $C_{1-6}$ alkyl group, a $C_{3-8}$ cycloalkyl group, a heterocycloalkyl group, an amino group, a mono($C_{1-6}$ alkyl)amino group, a di($C_{1-6}$ alkyl)amino group, a $C_{1-6}$ alkylamido group, a mono($C_{1-6}$ alkyl)aminoacyl group, a di($C_{1-6}$ alkyl)aminoacyl group, and a $C_{1-6}$ alkoxycarbonyl group;
$R^7$ and $R^8$ are each independently selected from the group consisting of hydrogen and a $C_{1-6}$ alkyl group;
the aryl group has 6-14 ring atoms;
the heteroaryl group has 5-12 ring atoms, in which 1-4 ring atoms are selected from the group consisting of N, O, and S;
the heterocycloalkyl group has 3-12 ring atoms, in which 1-3 ring atoms are replaced by atoms or groups selected from the group consisting of N, O, S, S(O), and S(O)$_2$; and
the heterocycloalkyloxy group has 3-12 ring atoms, in which 1-3 ring atoms are replaced by atoms or groups selected from the group consisting of N, O, S, S(O), and S(O)$_2$.

2. The compound or pharmaceutically acceptable salt thereof according to claim 1, wherein X is selected from the group consisting of —$NR^8$— and —S—.

3. The compound or pharmaceutically acceptable salt thereof according to claim 1, wherein n and m are each an integer of 0 to 3, and are not simultaneously 0.

4. The compound or pharmaceutically acceptable salt thereof according to claim 1, wherein $R^7$ and $R^8$ are hydrogen.

5. The compound or pharmaceutically acceptable salt thereof according to claim 1, wherein the ring Ar is a phenyl group.

6. The compound or pharmaceutically acceptable salt thereof according to claim 1, wherein p is an integer of 0 to 3.

7. The compound or pharmaceutically acceptable salt thereof according to claim 1, wherein q is an integer of 0 to 3.

8. The compound or pharmaceutically acceptable salt thereof according to claim 1, wherein $R^1$ is independently selected from the group consisting of a $C_{1-6}$ alkyl group, a $C_{2-6}$ alkenyl group, a $C_{2-6}$ alkynyl group, a halogen atom, an amino group, a hydroxy group, a $C_{1-6}$ alkoxy group, a $C_{1-6}$ alkylcarbonyl group, a cyano group, and a nitro group, wherein the $C_{1-6}$ alkyl group, $C_{1-6}$ alkoxy group, $C_{2-6}$ alkenyl group, and $C_{2-6}$ alkynyl group are optionally substituted by a halogen atom, a cyano group, a nitro group, a $C_{1-6}$ alkoxy group, an aryl group, a heteroaryl group, or a heterocycloalkyl group; and the aryl group, heteroaryl group, and heterocycloalkyl group are optionally further substituted by a halogen atom, a cyano group, a nitro group, a $C_{1-6}$ alkyl group, a $C_{1-6}$ alkoxy group, or a $C_{1-6}$ alkylcarbonyl group.

9. The compound or pharmaceutically acceptable salt thereof according to claim 8, wherein $R^1$ is independently selected from the group consisting of a $C_{2-6}$ alkynyl group, a halogen atom, a $C_{1-6}$ alkoxy group, and a $C_{1-6}$ alkylcarbonyl group, wherein the $C_{1-6}$ alkoxy group are optionally substituted by an aryl group, a heteroaryl group, or a heterocycloalkyl group; and the aryl group, heteroaryl group, and heterocycloalkyl group are optionally further substituted by a halogen atom, a cyano group, or a nitro group.

10. The compound or pharmaceutically acceptable salt thereof according to claim 9, wherein $R^1$ is independently selected from the group consisting of a $C_{2-6}$ alkynyl group, a halogen atom, a heteroaryl-substituted $C_{1-6}$ alkoxy group, an aryl-substituted $C_{1-6}$ alkoxy group, and a $C_{1-6}$ alkylcarbonyl group, wherein the aryl group and heteroaryl group are optionally further substituted by a halogen atom.

11. The compound or pharmaceutically acceptable salt thereof according to claim 10, wherein R¹ is independently selected from the group consisting of an ethynyl group, a halogen atom, a pyridyl-substituted $C_{1-6}$ alkoxy group, and a halophenyl-substituted $C_{1-6}$ alkoxy group.

12. The compound or pharmaceutically acceptable salt thereof according to claim 1, wherein R⁴, R⁵, and R⁶ are hydrogen.

13. The compound or pharmaceutically acceptable salt thereof according to claim 1, wherein R² is selected from the group consisting of hydrogen, a methoxy group, a tetrahydrofuranyloxy group, a methoxy-substituted ethoxy group, and a morpholinyl-substituted ethoxy group.

14. A compound represented by any one of following formulas or a pharmaceutically acceptable salt thereof:

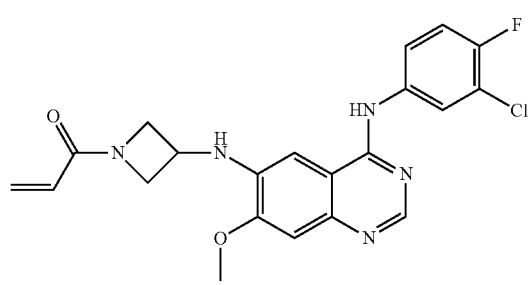

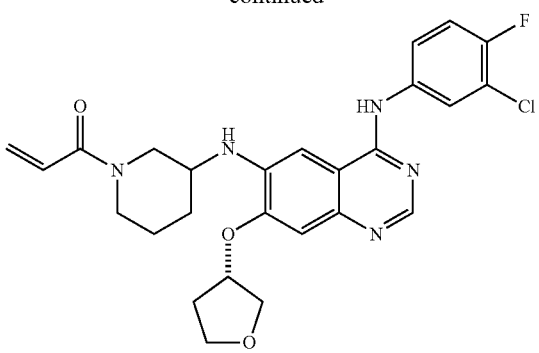

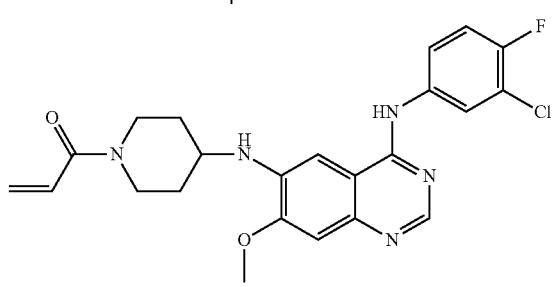

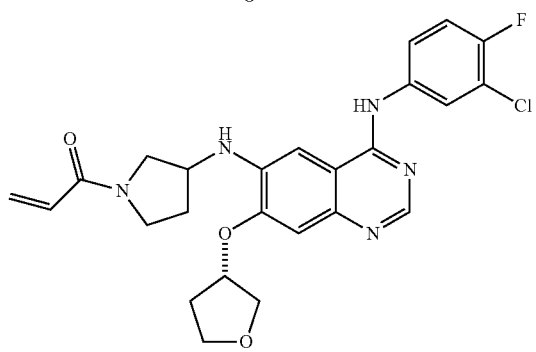

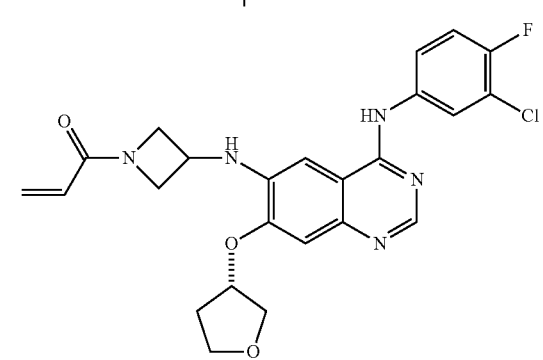

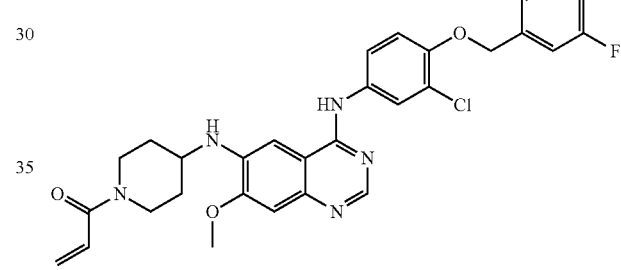

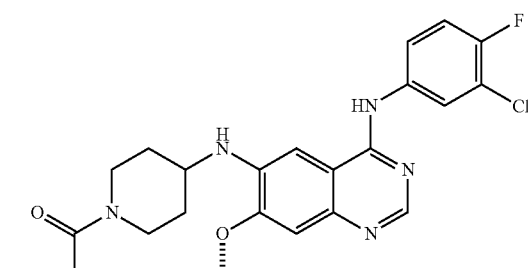

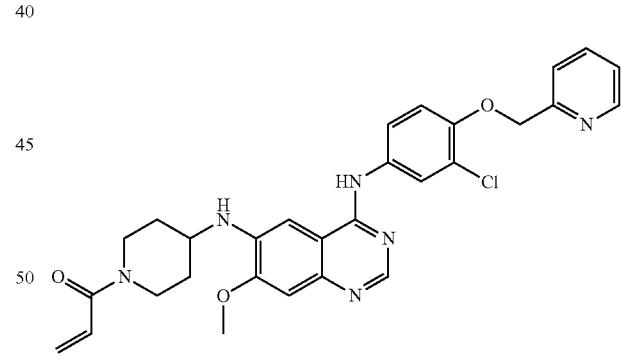

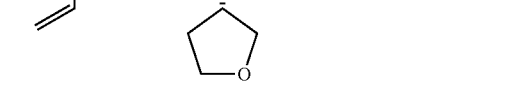

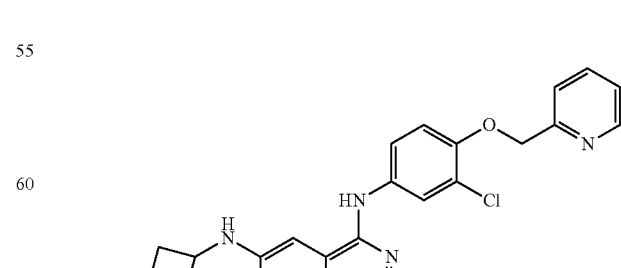

45
-continued
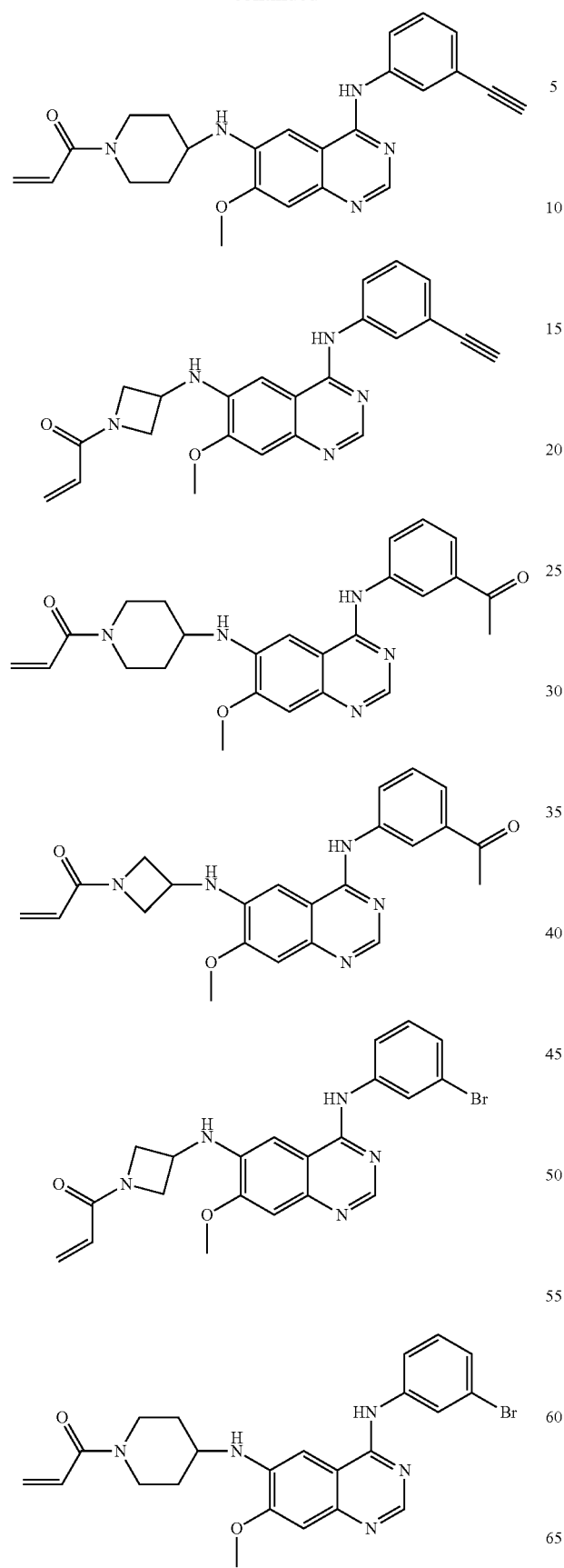
46
-continued
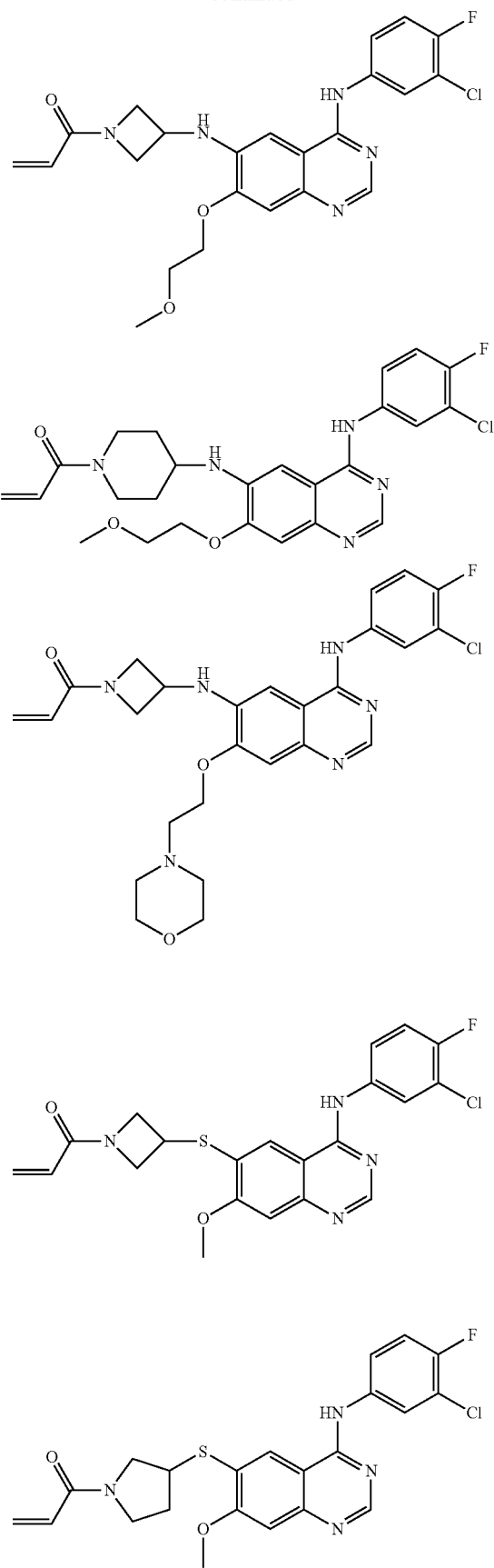

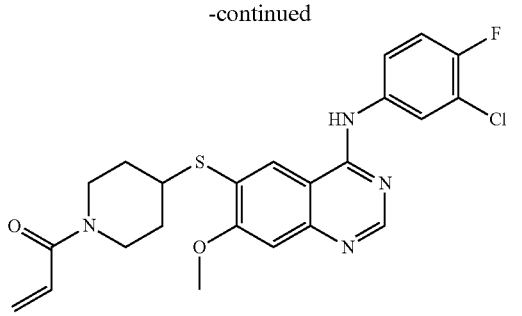

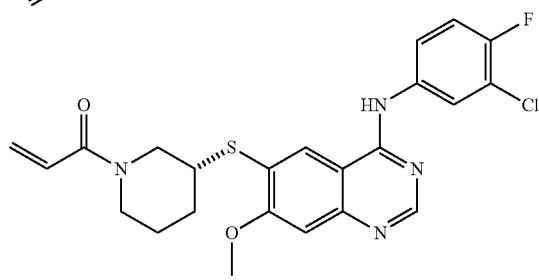

15. A pharmaceutical composition comprising the compound or pharmaceutically acceptable salt thereof according to claim 1, and a pharmaceutical acceptable carrier.

16. A method for inhibiting the growth of a cancer cell, comprising administering to a mammal in need thereof a therapeutic effective amount of the compound or pharmaceutically acceptable salt thereof according to claim 1;
    wherein the cancer cell is a lung cancer cell or a breast cancer cell.

* * * * *